(12) United States Patent
Stevens

(10) Patent No.: US 10,105,803 B1
(45) Date of Patent: Oct. 23, 2018

(54) CNC FIXTURE

(71) Applicant: Michael J. Stevens, State College, PA (US)

(72) Inventor: Michael J. Stevens, State College, PA (US)

(73) Assignee: Paradyne Technologies, Inc., State College, PA (US)

( * ) Notice: Subject to any disclaimer, the term of this patent is extended or adjusted under 35 U.S.C. 154(b) by 266 days.

(21) Appl. No.: 15/084,818

(22) Filed: Mar. 30, 2016

Related U.S. Application Data

(63) Continuation-in-part of application No. 13/959,686, filed on Aug. 5, 2013, now Pat. No. 9,327,374.

(Continued)

(51) Int. Cl.
  *B23B 41/12* (2006.01)
  *B23Q 3/06* (2006.01)
  (Continued)

(52) U.S. Cl.
  CPC .............. *B23Q 3/062* (2013.01); *B23B 41/12* (2013.01); *B23C 3/00* (2013.01); *B23Q 3/061* (2013.01);
  (Continued)

(58) Field of Classification Search
  CPC .......... B23Q 3/062; B23Q 3/061; B23Q 3/00; B23Q 1/66; B23C 2215/242; B23C 3/00;
  (Continued)

(56) References Cited

U.S. PATENT DOCUMENTS 5,212,857 A * 5/1993 McMurtry ............. B23Q 1/525
  29/38 C
5,741,111 A * 4/1998 Goostrey ............. B23Q 1/5456
  269/126

(Continued)

FOREIGN PATENT DOCUMENTS

JP   2011240466   * 12/2011
WO   WO 2011117818 A1 * 3/2011

OTHER PUBLICATIONS 5 axis CNC Shop Machining Center:Centroid PRI 2016; extracted from www.YouTube.com/user/CentroidCNC.*

(Continued)

*Primary Examiner* — Christopher M Koehler
*Assistant Examiner* — Mahdi H Nejad
(74) *Attorney, Agent, or Firm* — John J. Elnitski, Jr.

(57) ABSTRACT

A rotary head plate having a first precision surface and a second precision surface. The rotary head plate mounted to the first sub fixture. A second sub fixture being able to freely rotate with the rotary head plate when rotated. A tailstock plate mounted to the second sub fixture. The tailstock plate having a first precision surface and a second precision surface, A first head plate attached to the first precision surface of the rotary head plate and the first precision surface of the tailstock plate. A second head plate attached to the second precision surface of the rotary head plate and the second precision surface of the tailstock plate. The first head plate and second head plate adapted to each receive two cylinder heads. The first head plate and second head plate each including at least one cylinder head opening.

19 Claims, 43 Drawing Sheets

Related U.S. Application Data

(60) Provisional application No. 62/263,619, filed on Dec. 5, 2015, provisional application No. 61/680,060, filed on Aug. 6, 2012.

(51) Int. Cl.
 *B23C 3/00* (2006.01)
 *A61B 17/17* (2006.01)

(52) U.S. Cl.
 CPC ......... *A61B 17/17* (2013.01); *B23C 2215/242* (2013.01); *Y10T 29/4927* (2015.01); *Y10T 408/03* (2015.01); *Y10T 409/30868* (2015.01); *Y10T 409/305824* (2015.01)

(58) Field of Classification Search
 CPC ........... Y10T 409/30868; Y10T 408/00; Y10T 408/03; Y10T 29/4927; Y10T 409/305824; B23B 41/12
 USPC ................ 269/63, 71; 408/1 R; 409/219
 See application file for complete search history.

(56) References Cited

U.S. PATENT DOCUMENTS

| | | | |
|---|---|---|---|
| 2002/0006764 A1* | 1/2002 | Hanisch | B23Q 1/52 451/1 |
| 2002/0113354 A1* | 8/2002 | Mangelsen | B23Q 1/66 269/71 |
| 2007/0209185 A1* | 9/2007 | Huang | B23P 13/02 29/38 R |
| 2008/0315476 A1* | 12/2008 | Akhavan-Malayeri | B23Q 1/5437 269/20 |
| 2009/0110498 A1* | 4/2009 | Park | A61B 17/15 408/1 R |
| 2015/0202695 A1* | 7/2015 | Bruder | B23B 41/12 408/1 R |
| 2015/0258648 A1* | 9/2015 | Kubo | B23Q 1/66 29/559 |

OTHER PUBLICATIONS https://www.youtube.com/watch?v=wPJLePSxFe8; Nov. 13, 2010; CentroidCNC.*

* cited by examiner

CNC FIXTURE

This application is a continuation-in-part application of U.S. patent application Ser. No. 13/959,686 filed Aug. 5, 2013 and claims the benefit of and incorporates by reference U.S. Provisional Application No. 62/263,619 filed Dec. 5, 2015.

BACKGROUND

The present invention generally relates to computer controlled machining on computer controlled milling machines. More specifically, the present invention relates to a CNC fixture used with a computer controlled milling machine to hold and manipulate the position of a work piece.

The industry of milling out engine blocks and cylinder heads of fossil fuel engines is growing exponentially. This is due to the increase in demand of high performance engines. The demand for high performance engine also includes the demand for high precision. Currently, there are no CNC fixtures to keep up with the demand for the milling of matching engine blocks and cylinder heads quickly. Usually, the same milling machine is used to mill both the engine block and the matching cylinder head. That requires the install and removal of each of the engine block and the cylinder head on the same milling machine, which takes a large amount of set up time. What is needed is a fixture to hold and manipulate the engine block and the cylinder head that allows for quick and precise install and removal of the engine block and the cylinder head.

It is an object of the present invention to provide a fixture to hold and manipulate an engine block and cylinder head that allows for quick and precise install and removal of the engine block and the cylinder head.

SUMMARY

A fixture for a milling machine to position and manipulate related work pieces. A rotary head plate having a first precision surface and a second precision surface. A first sub fixture being powered to rotate the rotary head plate. The rotary head plate mounted to the first sub fixture such that the rotary head plate is rotated by the first sub fixture. A second sub fixture being able to freely rotate with the rotary head plate when rotated. A tailstock plate mounted to the second sub fixture, where the tailstock plate is freely rotatable with the rotary head plate when the rotary head plate is rotated. The tailstock plate having a first precision surface and a second precision surface. A first head plate attached to and between the first precision surface of the rotary head plate and the first precision surface of the tailstock plate. The first head plate adapted to receive two cylinder heads and the first head plate including at least one cylinder head opening. A second head plate attached to and between the second precision surface of the rotary head plate and the second precision surface of the tailstock plate. The second head plate adapted to receive two cylinder heads and the second head plate including at least one cylinder head opening. The tailstock plate capable of rotating with the rotary plate due to attachment of the first head plate and the second head plate.

DETAILED DESCRIPTION

Figure 1:
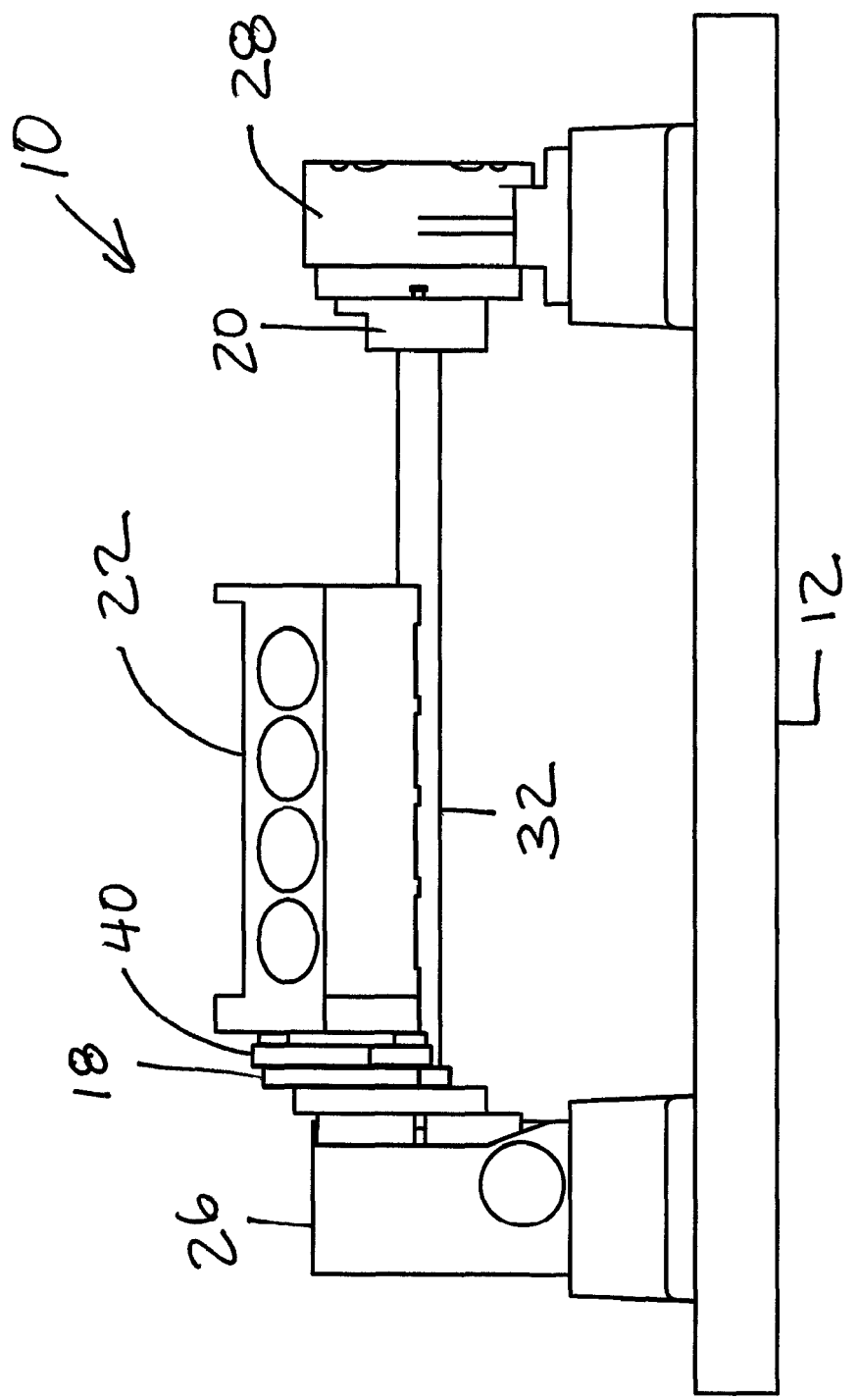
FIG. 1 is a side view of a fixture according to the present invention.
Figure 2:
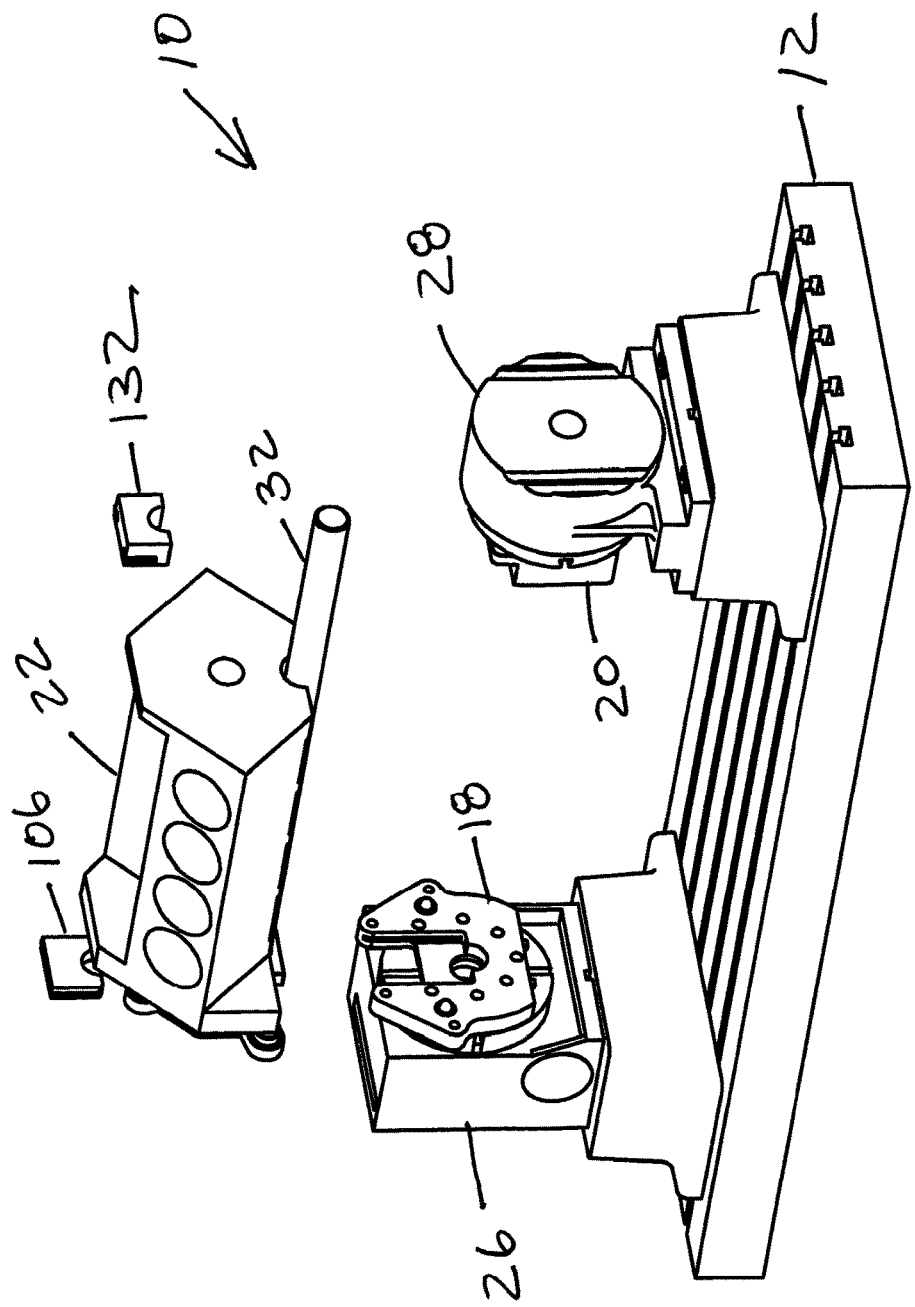
FIG. 2 is a perspective view of the fixture of FIG. 1 according to the present invention.
Figure 3:
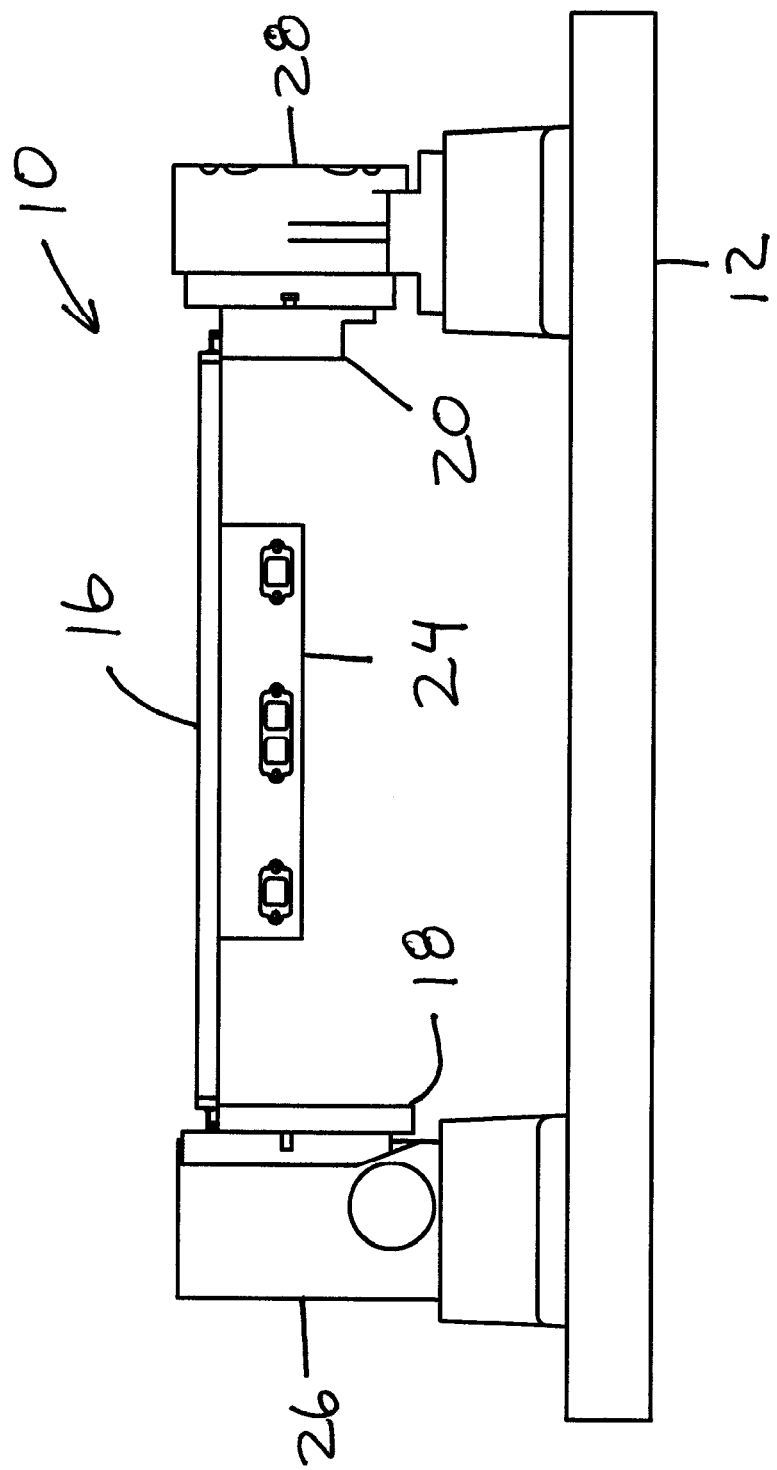
FIG. 3 is a side view of a fixture according to the present invention.
Figure 4:
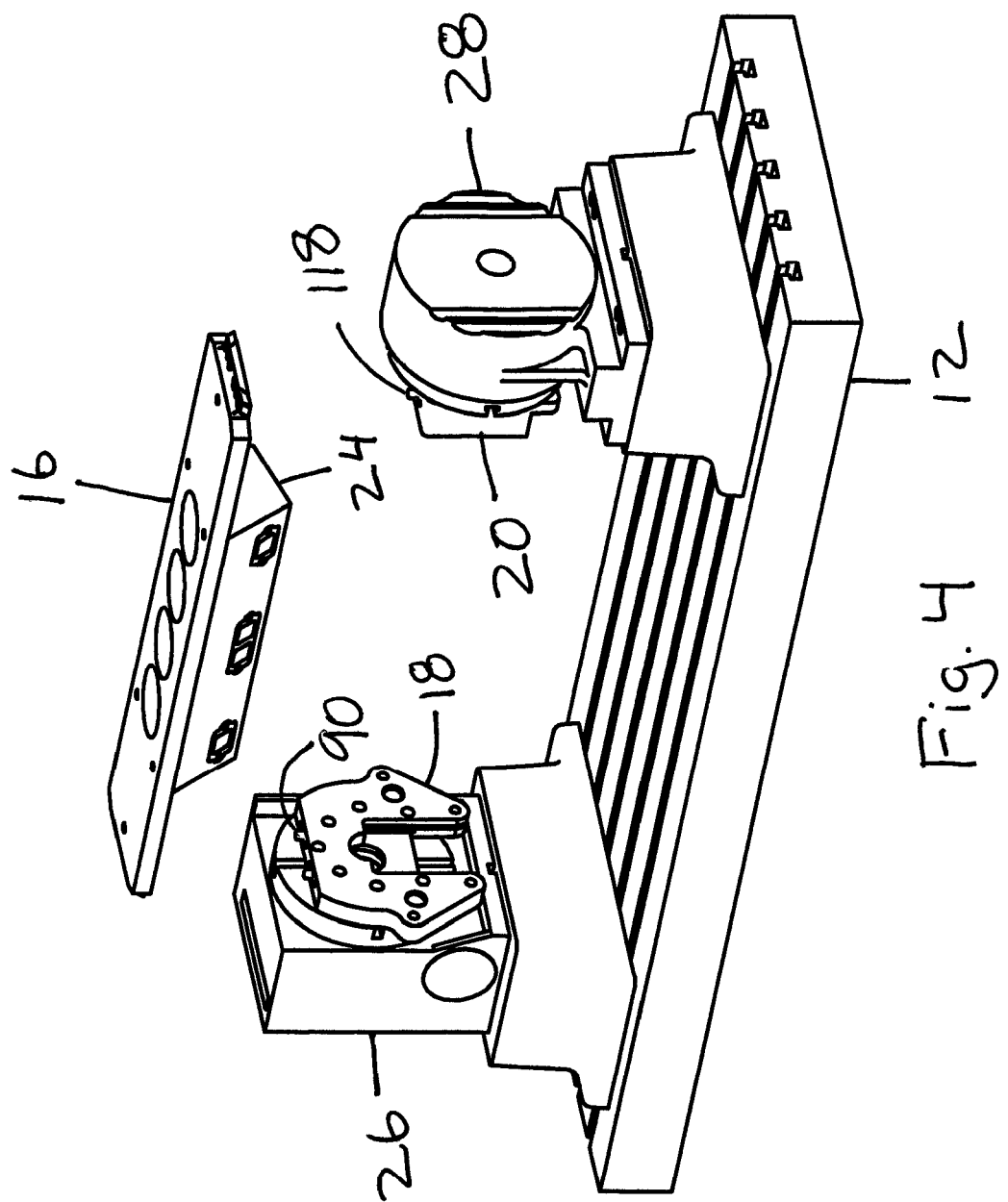
FIG. 4 is a perspective view of the fixture of FIG. 2 according to the present invention.

The present invention is a CNC fixture for quick change mounting of cylinder heads and engine blocks as work pieces during CNC machining operations. The CNC fixture 10 is shown in FIGS. 1-4. The CNC fixture 10 includes a base 12, a first sub fixture and second sub fixture attached to the base, block bar assembly 14, head plate 16, rotary plate 18 and tailstock plate 20. FIGS. 1-2 show the CNC fixture 10 with the block bar assembly 14 and FIGS. 3-4 show the CNC fixture 10 with the head plate 16. The block bar assembly 14 is for mounting of the engine block 22. The head plate 16 is for mounting of the cylinder head 24. The base 12 is for mounting and supporting the CNC fixture 10 to a milling machine. The base 12 is usually a horizontal table of the milling machine. The first sub fixture is shown as a powered rotary table 26 attached to the base 12. The rotary table 26 is servo powered to be able to rotate and position the work piece thru 360 degrees of rotation about the axis between the first sub fixture and second sub fixture. The second sub fixture is shown as a non-powered rotating tailstock 28 attached to the base 12, which is in line with the powered rotary table 26. The tail stock 28 is a free rotating assembly with a brake to provide support for the work piece in alignment with the rotational axis of the rotary table 26. The position of the engine block 22 or cylinder head 24 about the axis between the first sub fixture and the second sub fixture is controlled by the rotary table 26.

Figure 5:
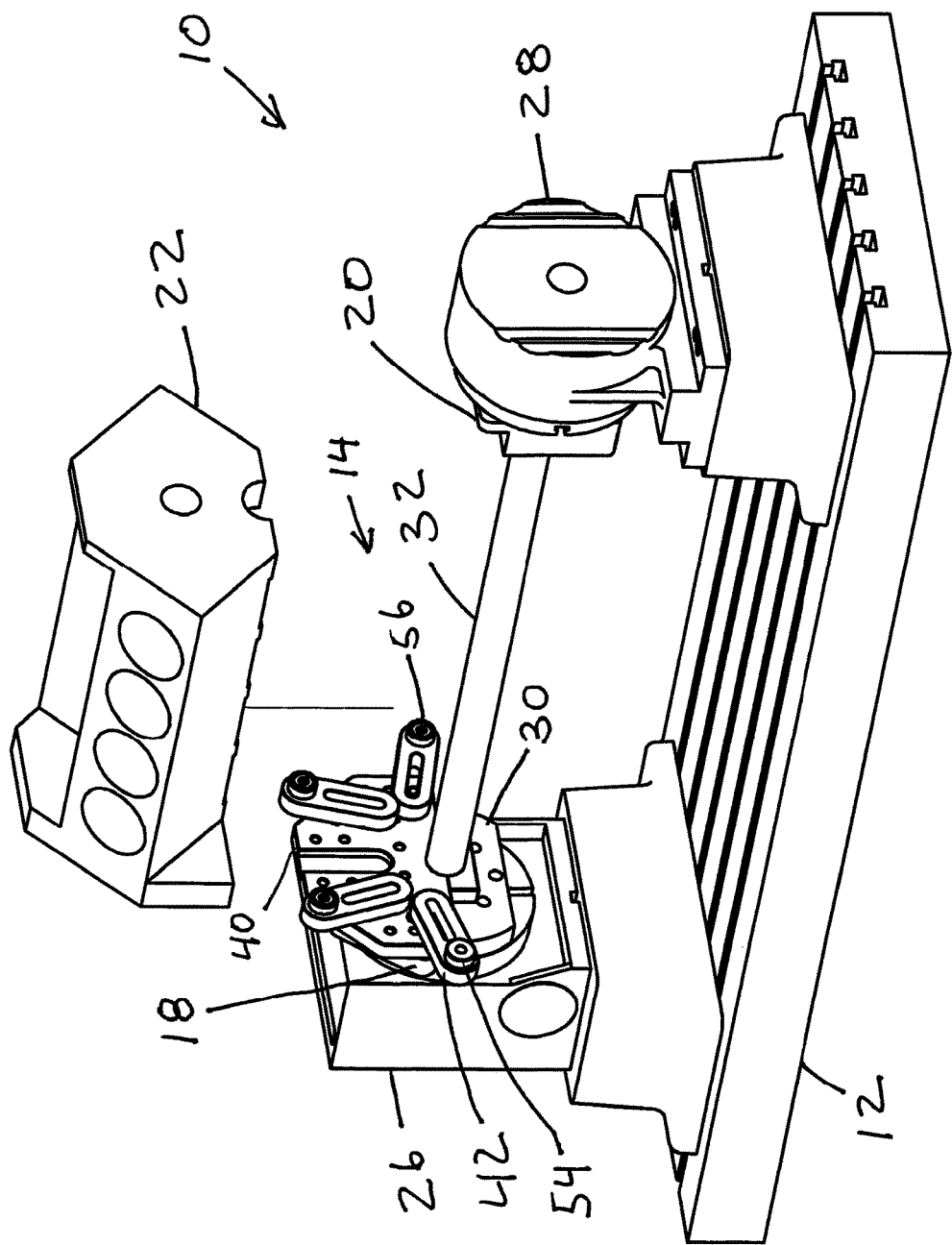
FIG. 5 is an exploded perspective view of the fixture of FIG. 1 according to the present invention.
Figure 6:
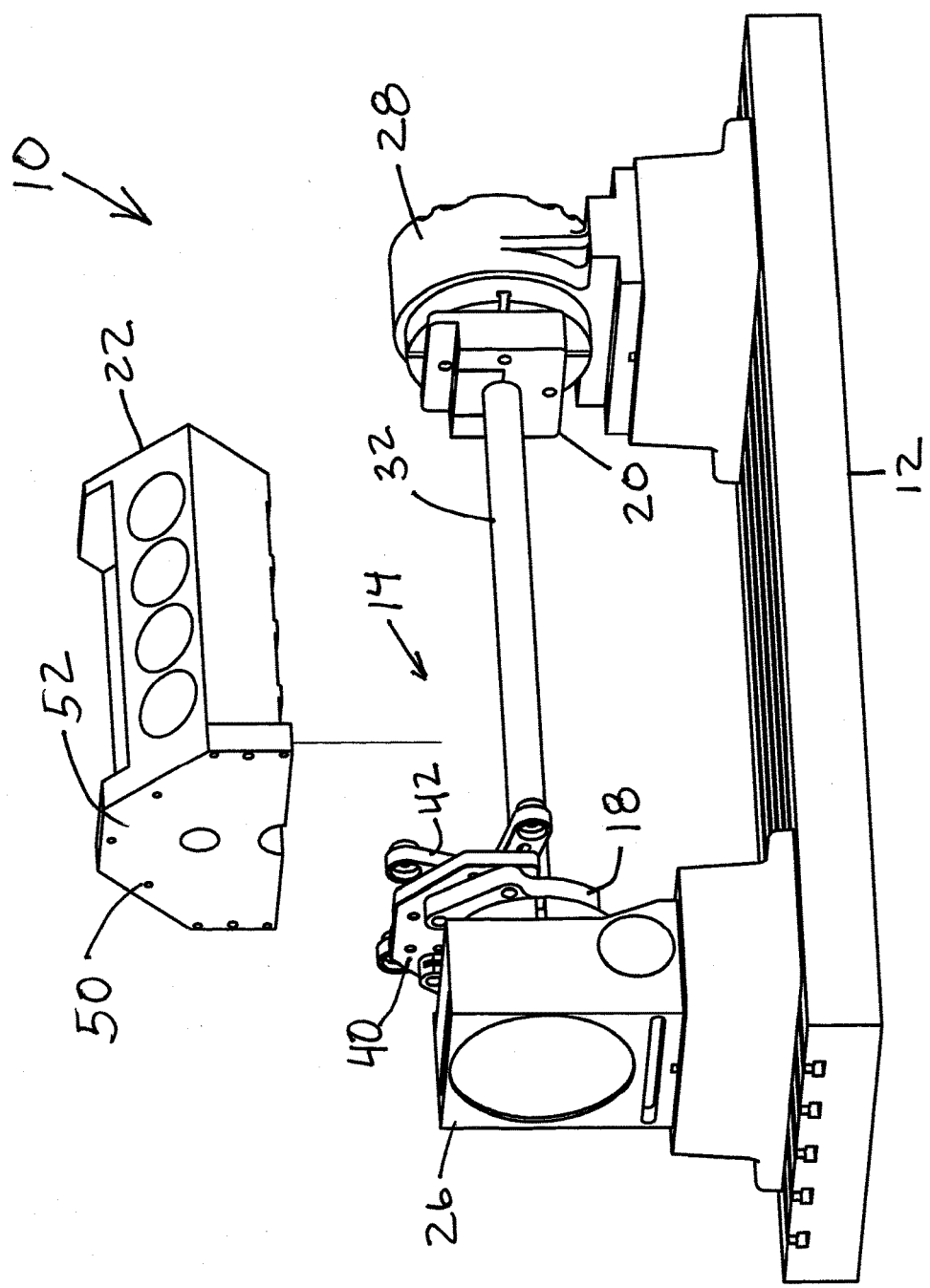
FIG. 6 is an exploded perspective view of the fixture of FIG. 1 according to the present invention.
Figure 7:
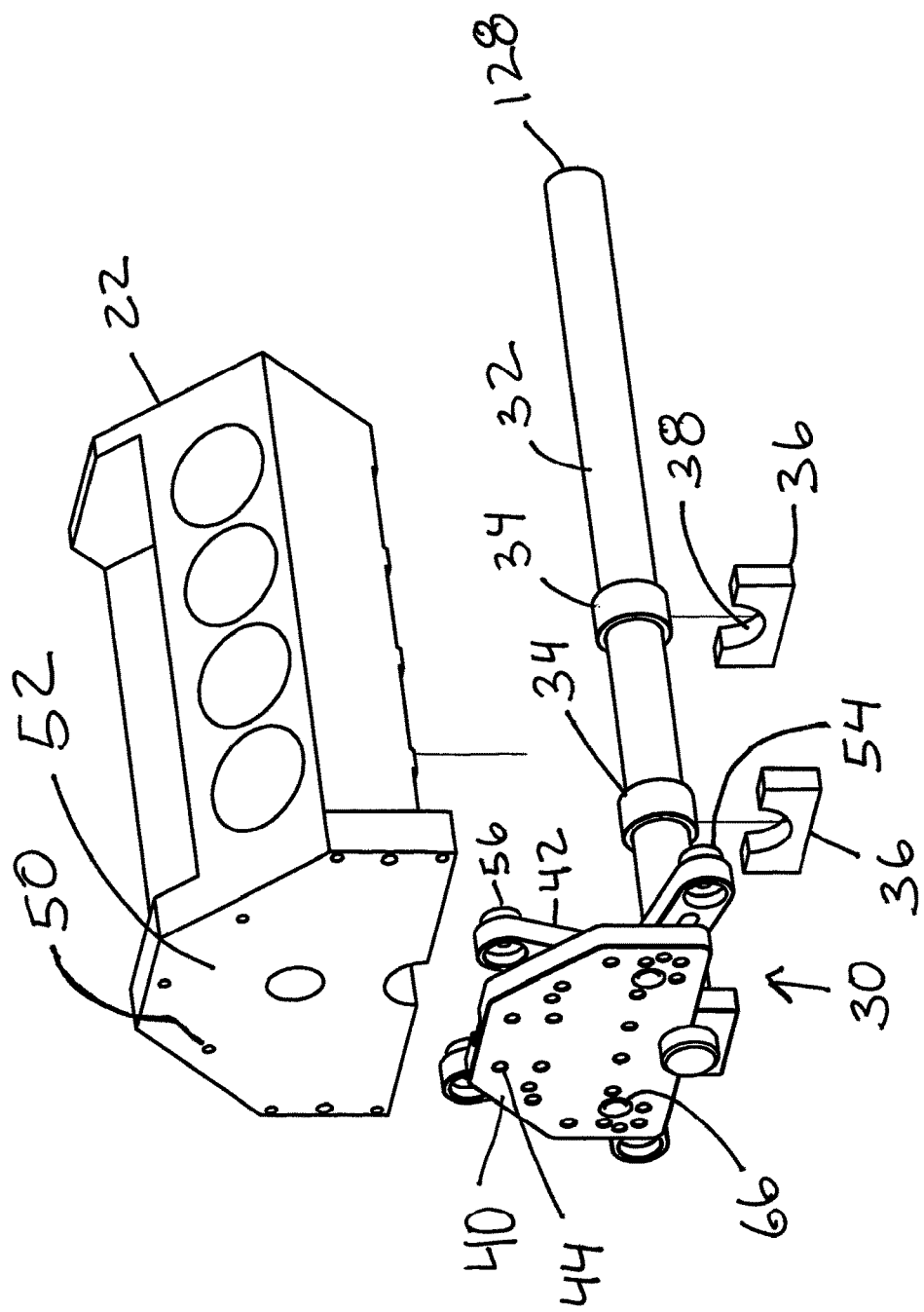
FIG. 7 is an exploded perspective view of a block bar assembly according to the present invention.
Figure 8:
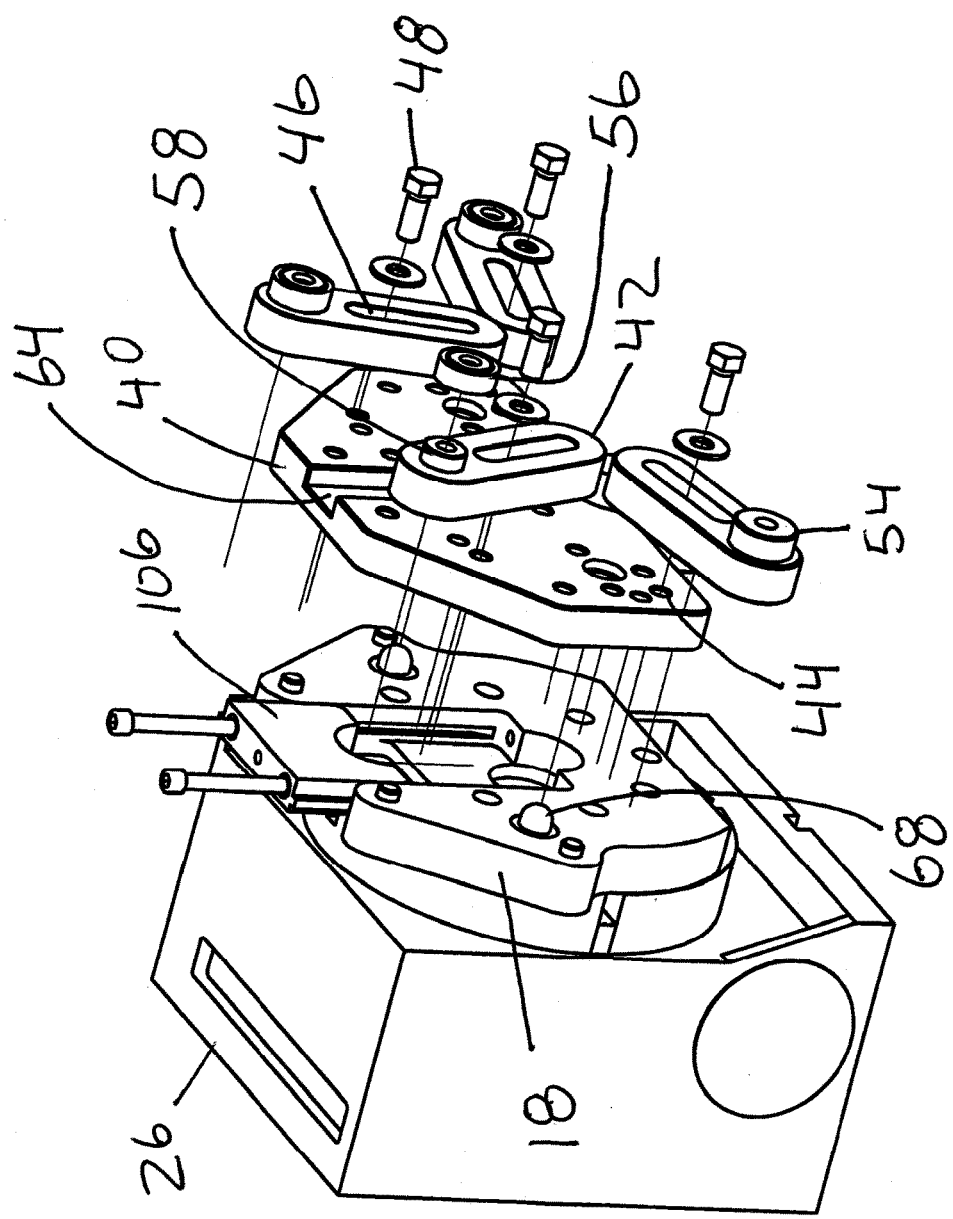
FIG. 8 is an exploded perspective view of a block mount according to the present invention.
Figure 9:
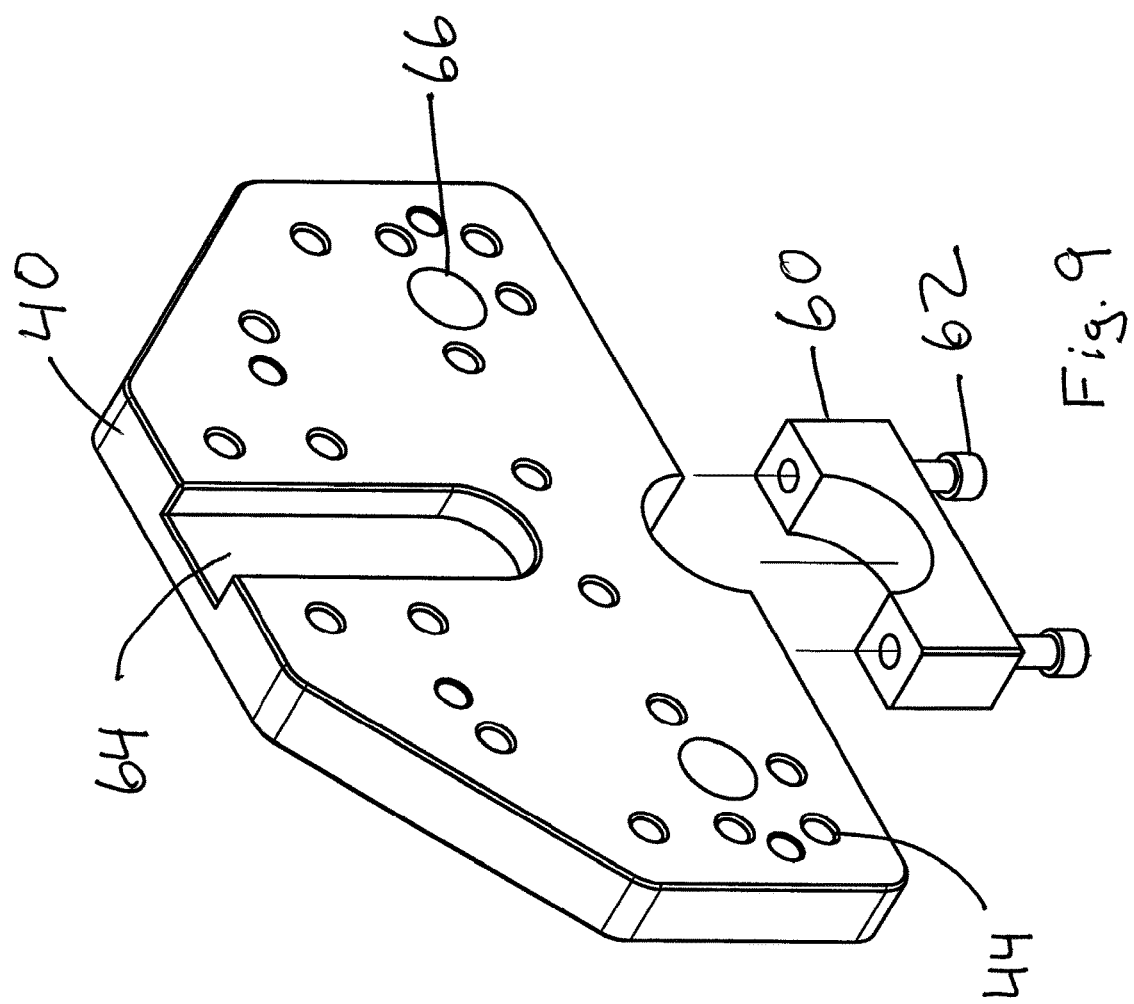
FIG. 9 is another perspective view of the block mount according to the present invention.
Figure 10:
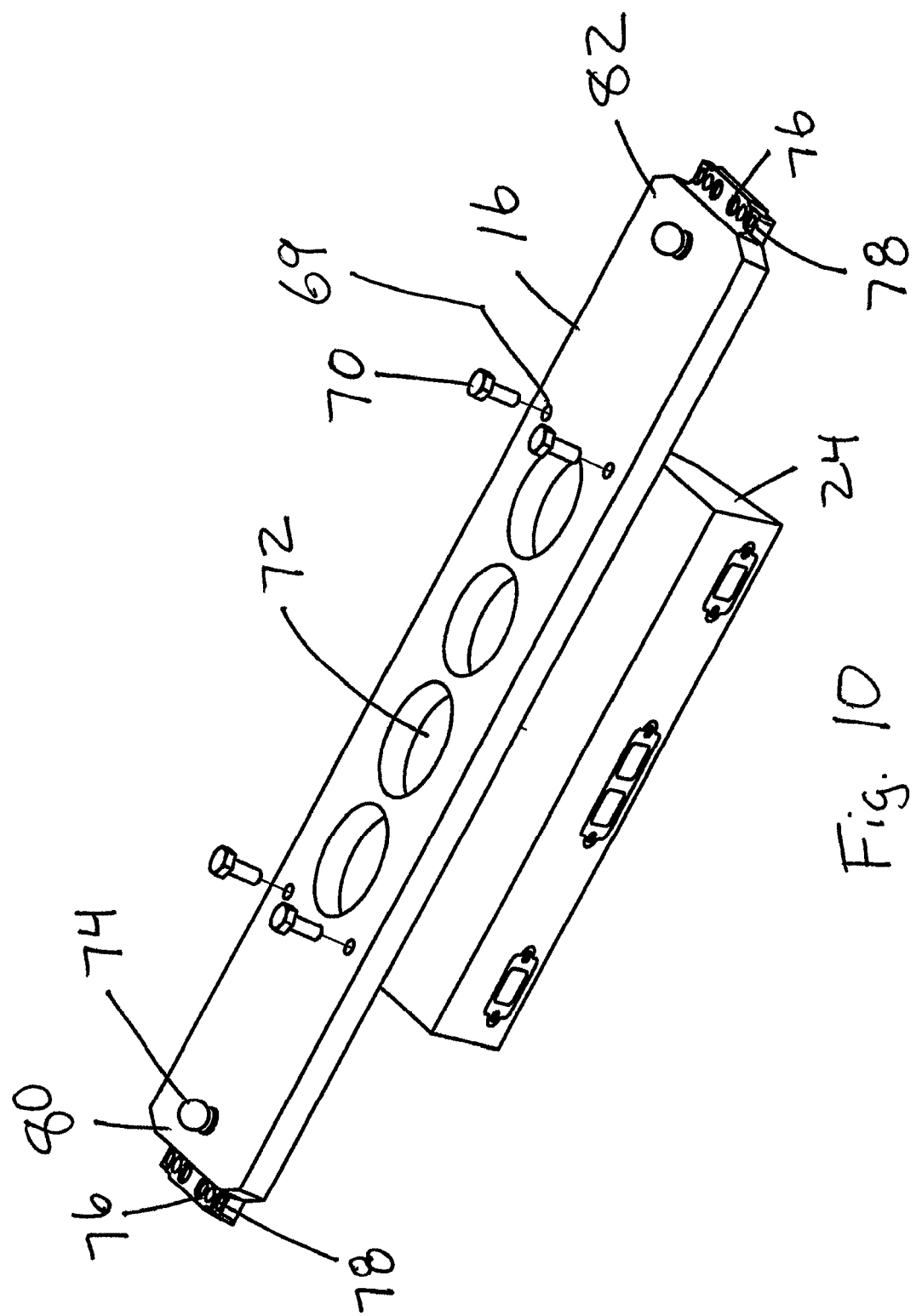
FIG. 10 is an exploded perspective view of a head plate according to the present invention.

The block bar assembly 14 is for attachment and support of the engine block 22 to be milled as the work piece, as shown in FIGS. 5-7. The block bar assembly 14 includes a block mount 30 secured to a precise round bar 32, as shown in FIGS. 8-9. The bar 32 fits into the crank shaft channel of the engine block 22, such that engine block 22 rests on the bar 32. FIG. 7 shows bar spacers 34 and bar clamps 36. The bar spacers 34 are placed on the bar 32, if needed to accommodate the size of the crank shaft channel. The bar clamps 36 include a bar cut out 38 to go around the bar 32. The bar clamps 36 pin the bar 32 against the engine block 22 and hold the engine block 22 in place on the bar 32. The block mount 30 is a combination of a block plate 40 and adjustment arms 42. The block plate 40 includes threaded bolt holes 44 to attach the adjustment arms 42 to the block plate 40, as shown in FIG. 8. The adjustment arms 42 each include an arm slot 46 to receive bolts 48 that secure adjustment arms 42 to the block plate 40. The arm slot 46 allows for positioning of the adjustment arm 42 to match the bolt holes 50 on the front face 52 of the engine block 22. One adjustment arm 42 has a fixed arm spacer 54 to provide space between the adjustment arms 42 and the engine block 22. The other adjustment arms 42 have an adjustable spacer 56 that includes a threaded stud 58 to receive the adjustable spacer 56. The adjustable spacer 56 is threaded towards or away from the adjustment arm 42 on the threaded stud 58 to adjust how much the adjustable spacer 56 extends out from the adjustable arm 42. The front face 52 of an engine block 22 may not be exactly parallel to the block plate 40 and the adjustable spacer 56 compensates for any irregularities of the front face 52. The block plate 40 includes a clamp 60 to clamp about the bar 32 at the block plate 40, as shown in FIG. 9. The clamp 60 is held in place using two bolts 62 that thread into the block plate 40. The block plate 40 includes a cam shaft slot 64 to receive an end of a cam shaft, if present. Note, FIG. 7 shows the bar 32 extending beyond the block plate 40 for mounting to the rotary plate 18. The block plate 40 also includes two alignment pin holes 66 to receive alignment pins 68 from the rotary plate 18. The head plate 16 is for attachment and support of the cylinder head 24 to be milled as the work piece, as shown in FIG. 10. The head plate 16 includes bolt holes 69 to receive bolts 70 that screw into the cylinder head 24. The head plate 16 includes cylinder openings 72 to allow access to the cylinder head 24. The head plate 16 includes tooling balls 74 to act as known reference points during setup for milling operations. The head plate 16 includes dowel holes 76 and bolt holes 78 at a first end 80 and a second end 82 of the head plate 16.

Figure 11:
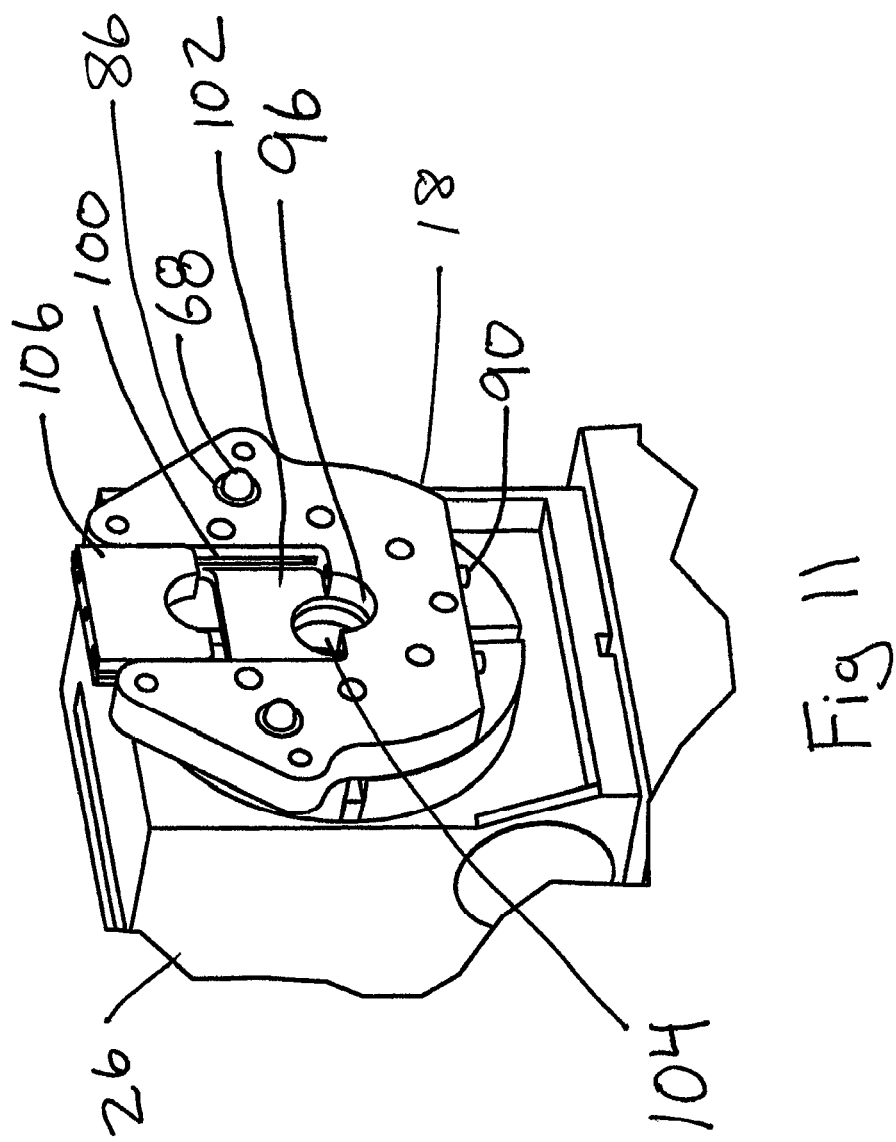
FIG. 11 is a perspective view of a rotary plate according to the present invention.
Figure 12:
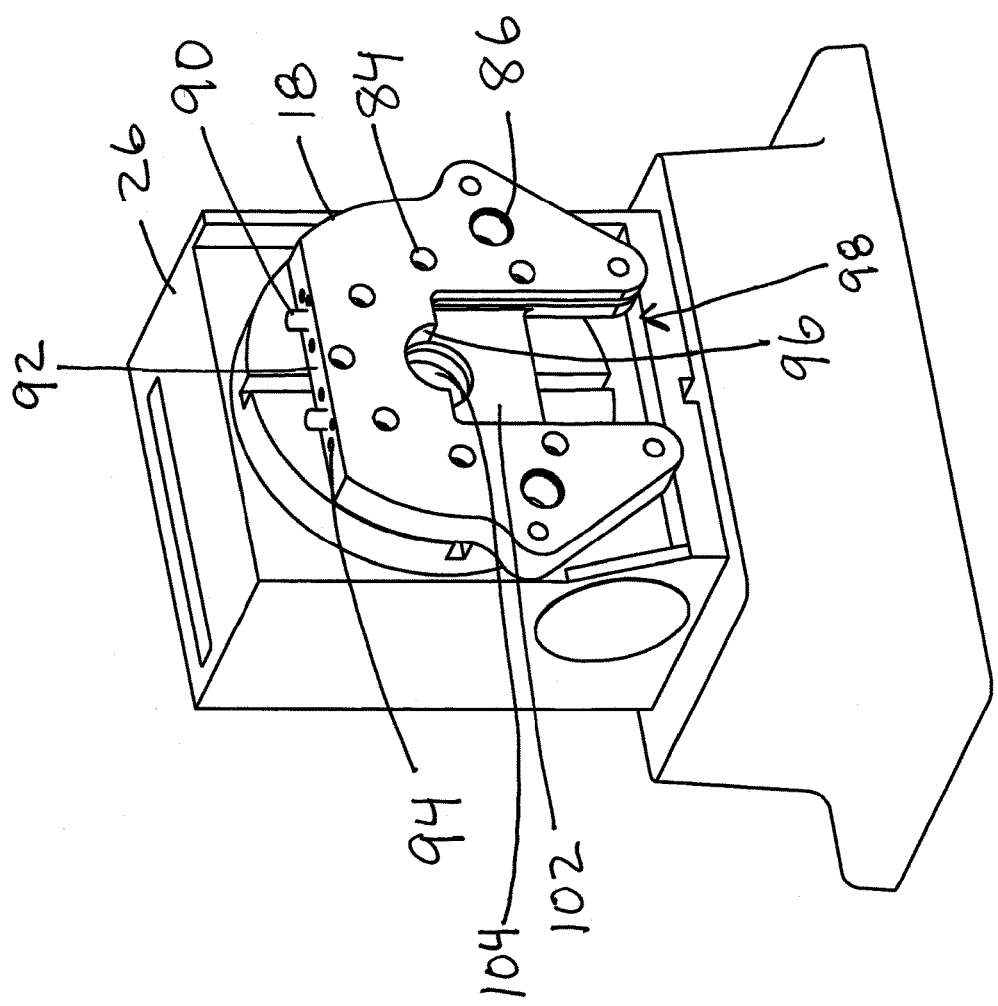
FIG. 12 is another perspective view of a rotary plate according to the present invention.
Figure 13:
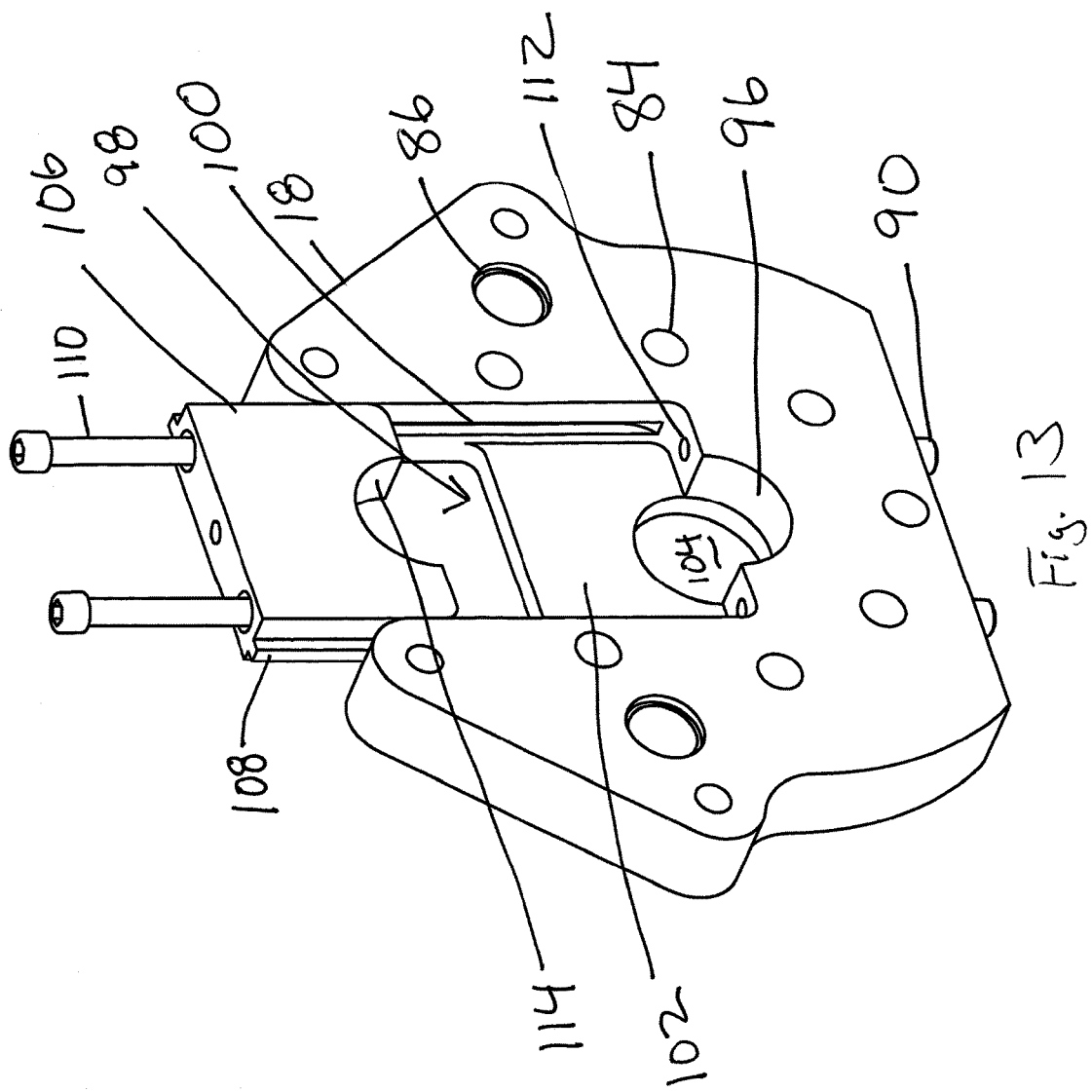
FIG. 13 is another perspective view of a rotary plate according to the present invention.

The rotary plate 18 attaches to the powered rotary table 26. FIGS. 11-13 show the rotary plate 18. The rotary plate 18 includes bolt holes 84 and alignment pin holes 86 that align the alignment pin holes 66 of the block plate 40. The alignment pin holes 86 are to receive alignment pins 68. The bolt holes 84 are for bolting the rotary plate 18 to rotary table 26. The rotary plate 18 includes two reference dowels 90 extending from a first precision surface 92 and threaded bolt holes 94 in the first precision surface 92. The dowels 90 and first precision surface 92 are for receiving the head plate 16. The bolt holes 94 are for securing the head plate 16 to the rotary plate 18 at the first precision surface 92. The rotary plate 18 includes a second precision surface 96 shown as a semicircular channel. The rotary plate 18 includes a clamp opening 98 above the second precision surface 96 of the rotary plate 18. The clamp opening 98 includes slots 100 and back plate 102 with a round opening 104. The round opening 104 is for receiving the bar 32. The rotary plate 18 includes a clamping plate 106 having tongues 108 that match up with slots 100 of the clamp opening 98, so that the clamping plate 106 can be placed into the clamp opening 98. The clamping plate 106 is bolted into place using bolts 110 and threaded holes 112 on the rotary plate 18. The clamping plate 106 includes a semicircular channel 114 that matches the semicircular channel of the second precision surface 96 to form a round opening that clamps around the bar 32 when the clamping plate 106 is secured to the rotary plate 18.

Figure 14:
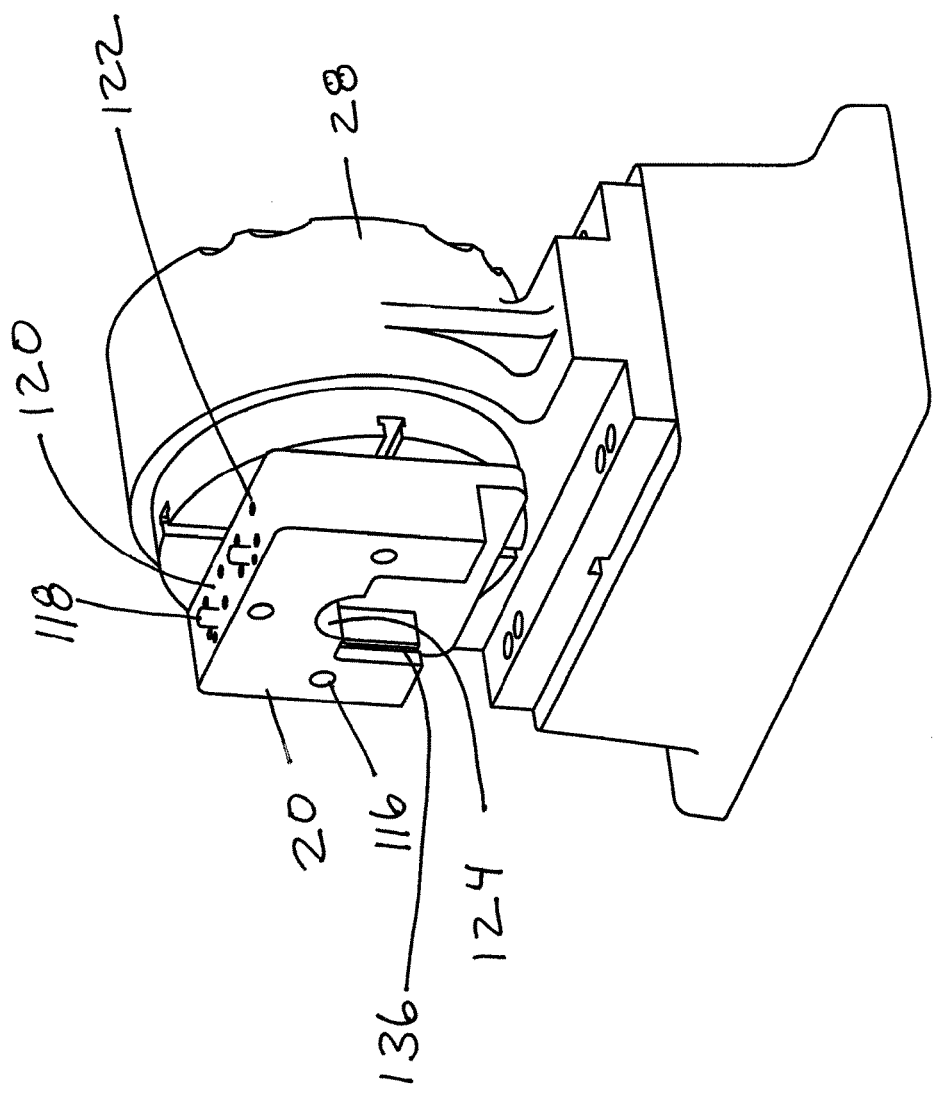
FIG. 14 is a perspective view of a tailstock plate according to the present invention.
Figure 15:
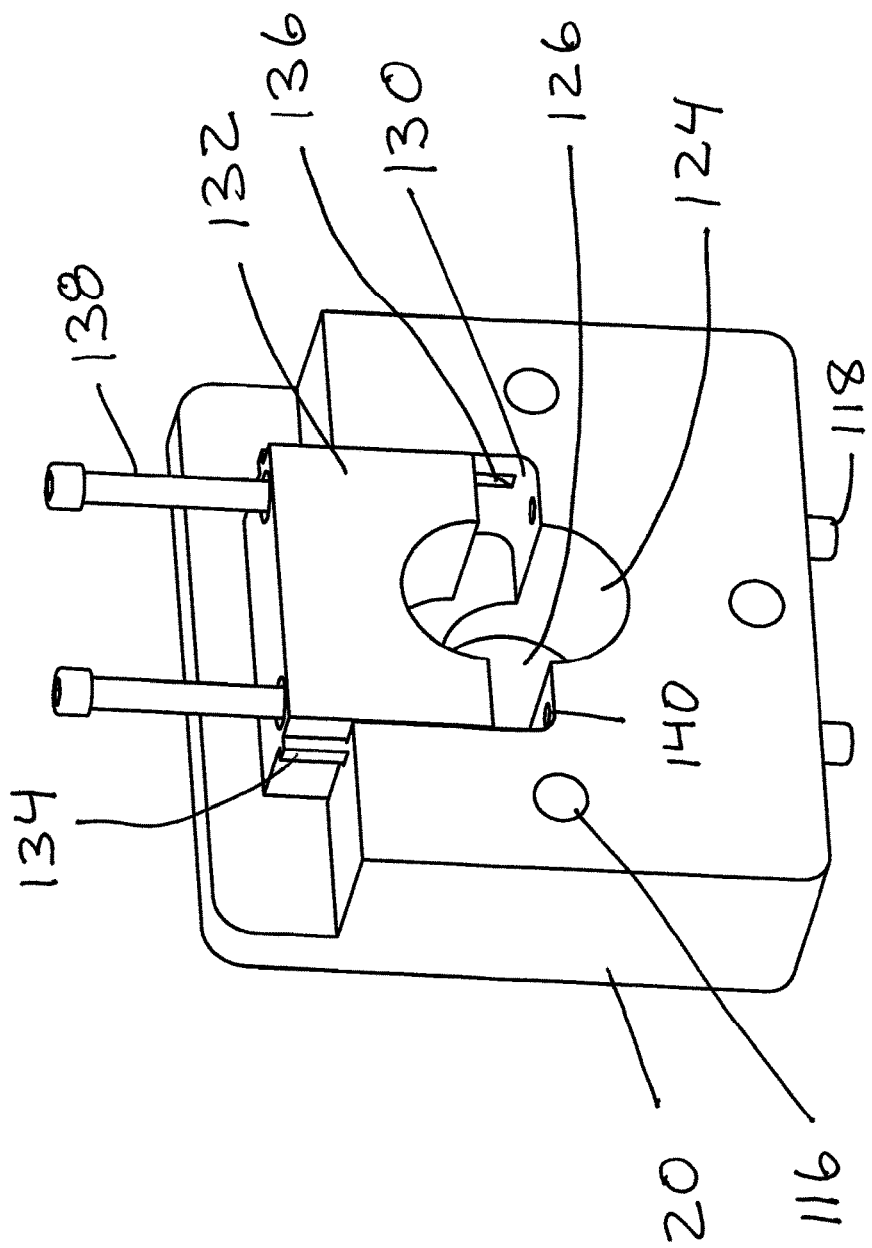
FIG. 15 is another perspective view of a tailstock plate according to the present invention.
Figure 16:
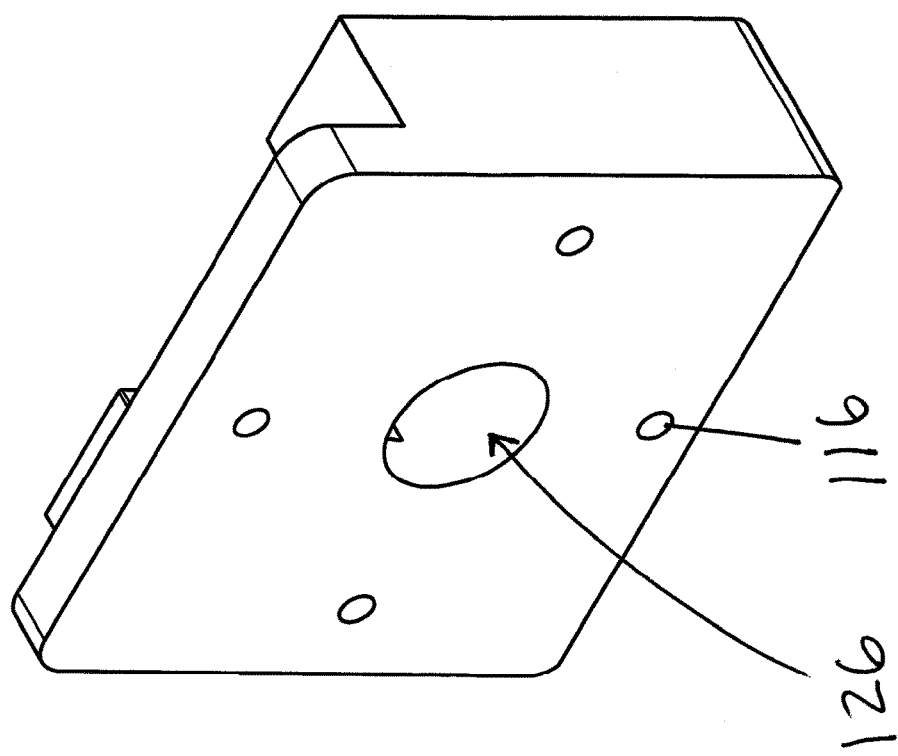
FIG. 16 is another perspective view of a tailstock plate according to the present invention.
Figure 17:
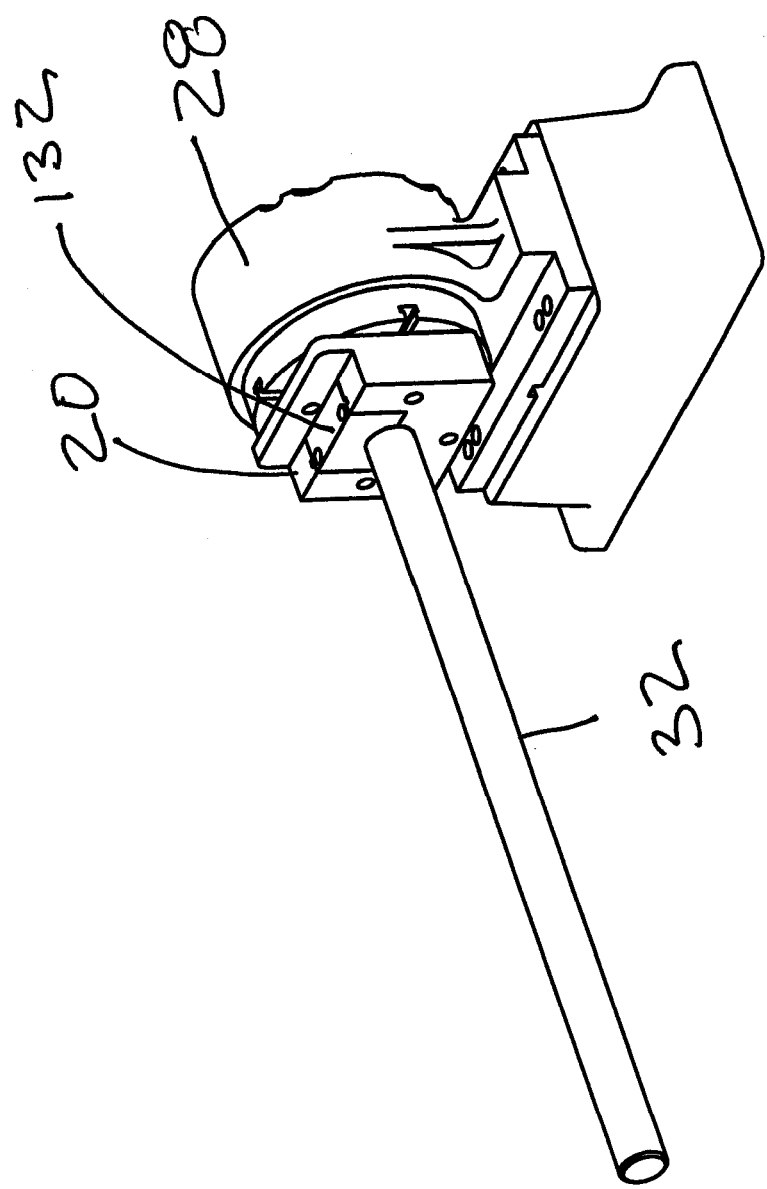
FIG. 17 is a perspective view of a tailstock plate with a bar according to the present invention.
Figure 18:
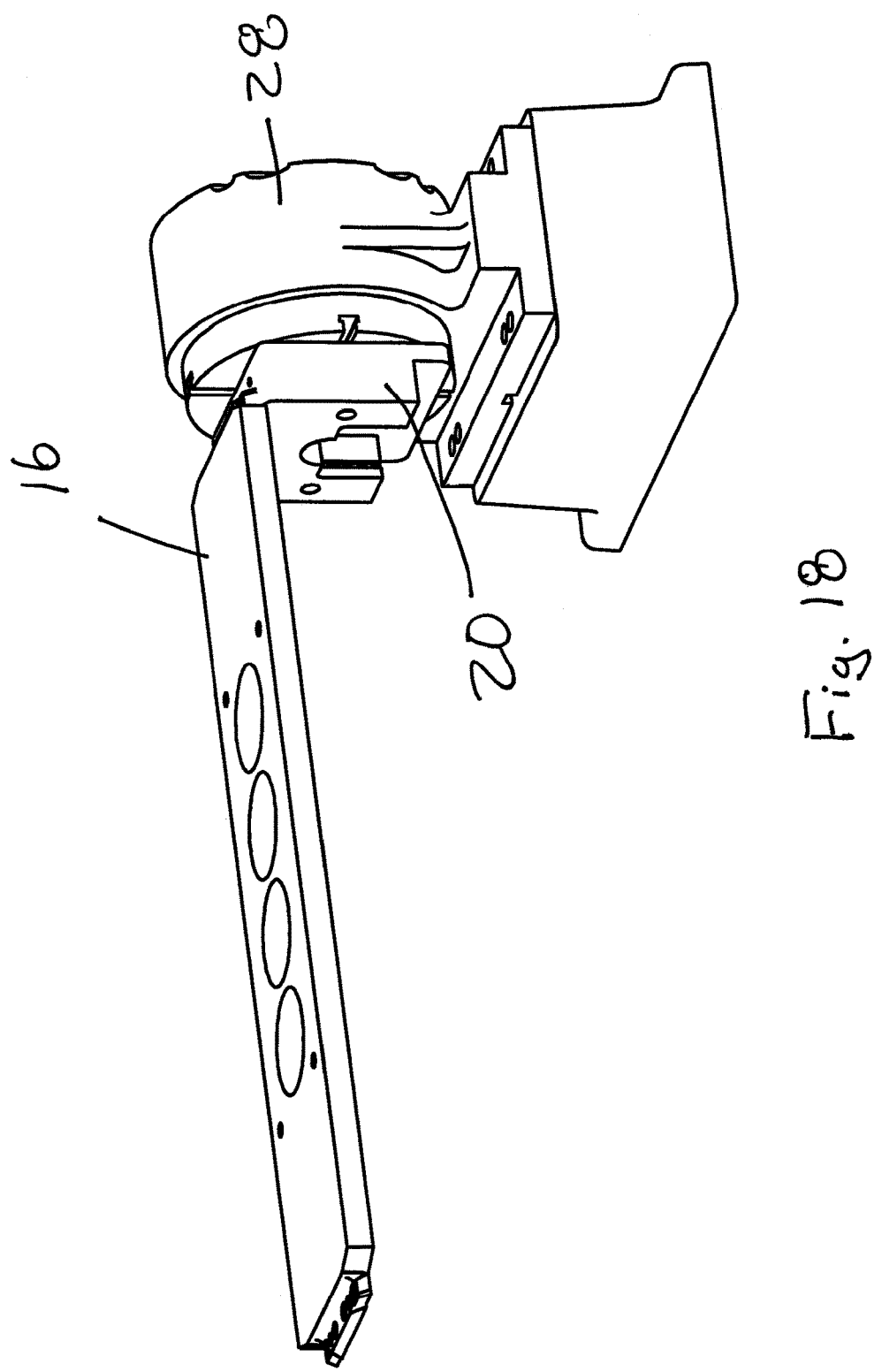
FIG. 18 is a perspective view of a tailstock plate with a head plate according to the present invention.
Figure 19:
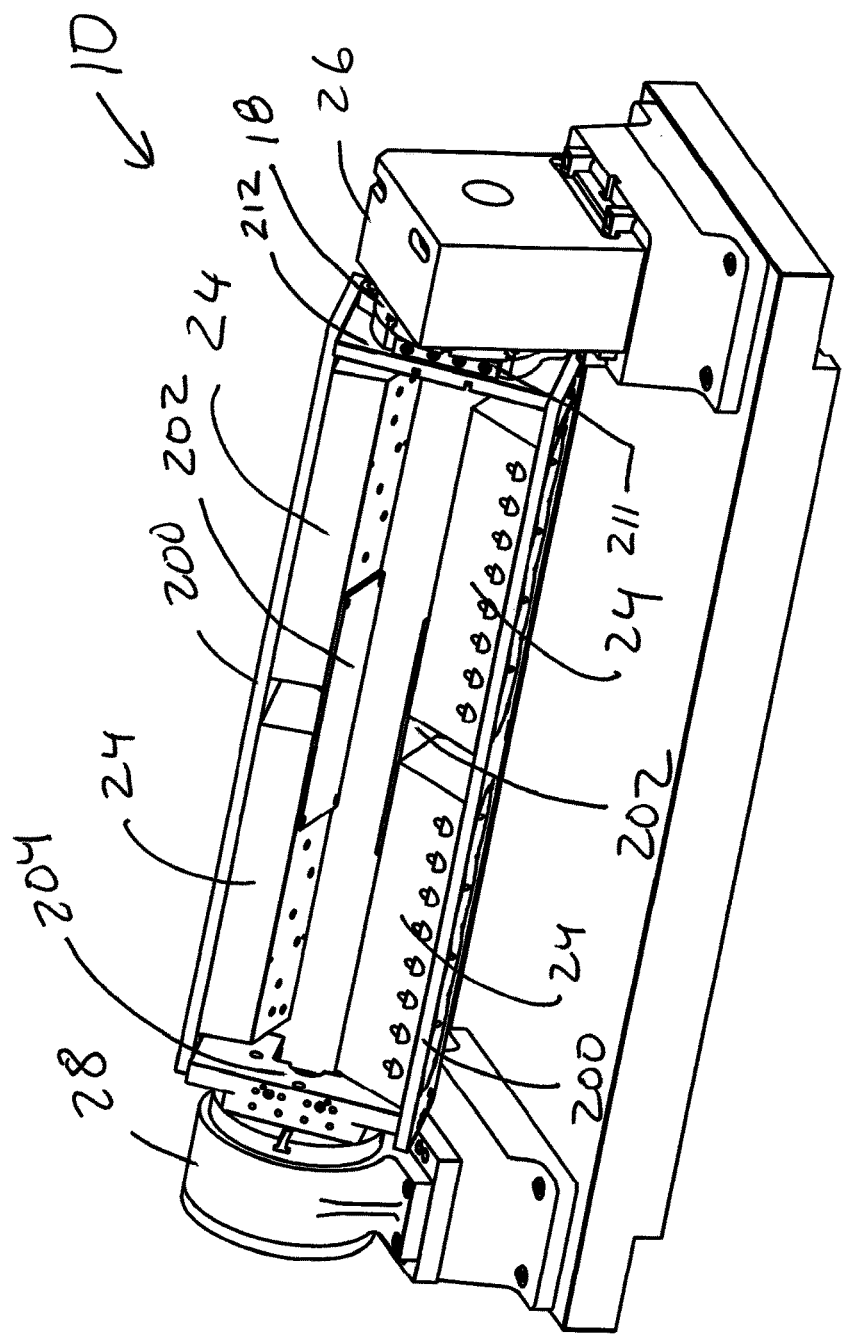
FIG. 19 is a perspective view of a fixture with two head plates according to the present invention.
Figure 20:
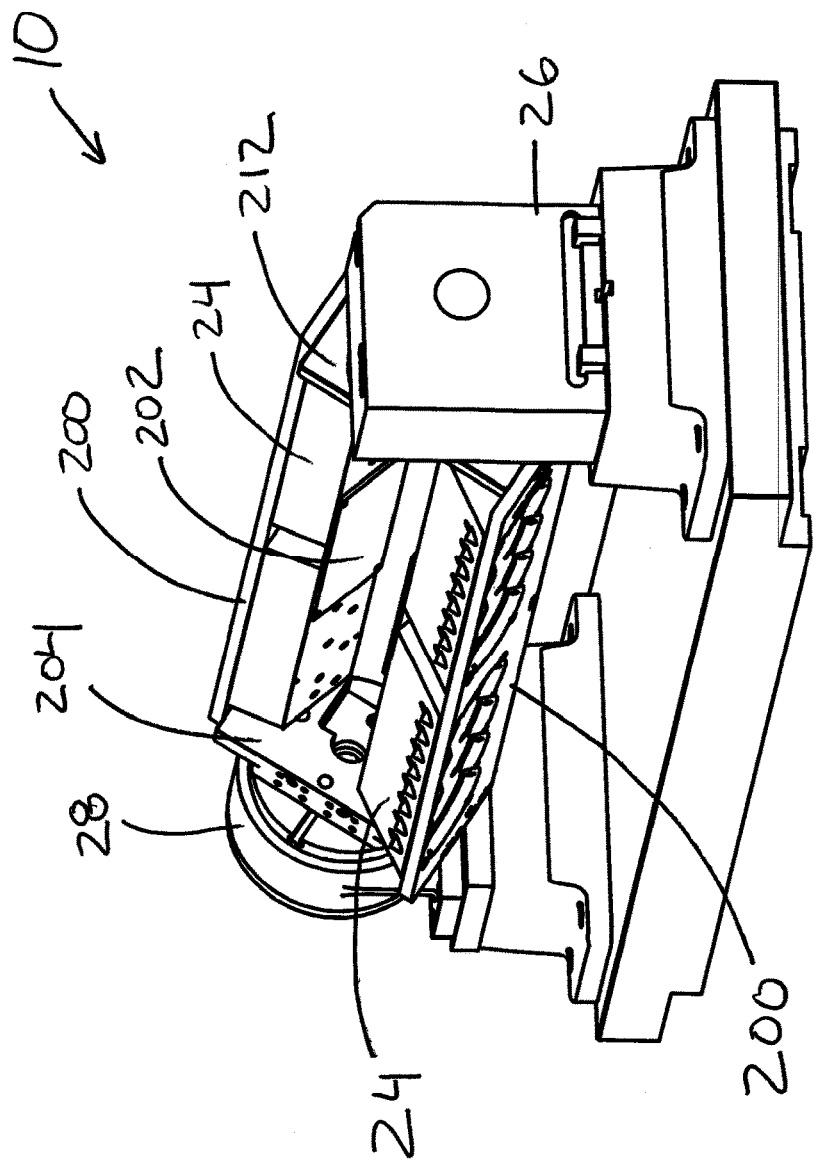
FIG. 20 is a perspective view of a fixture with two head plates according to the present invention.
Figure 21:
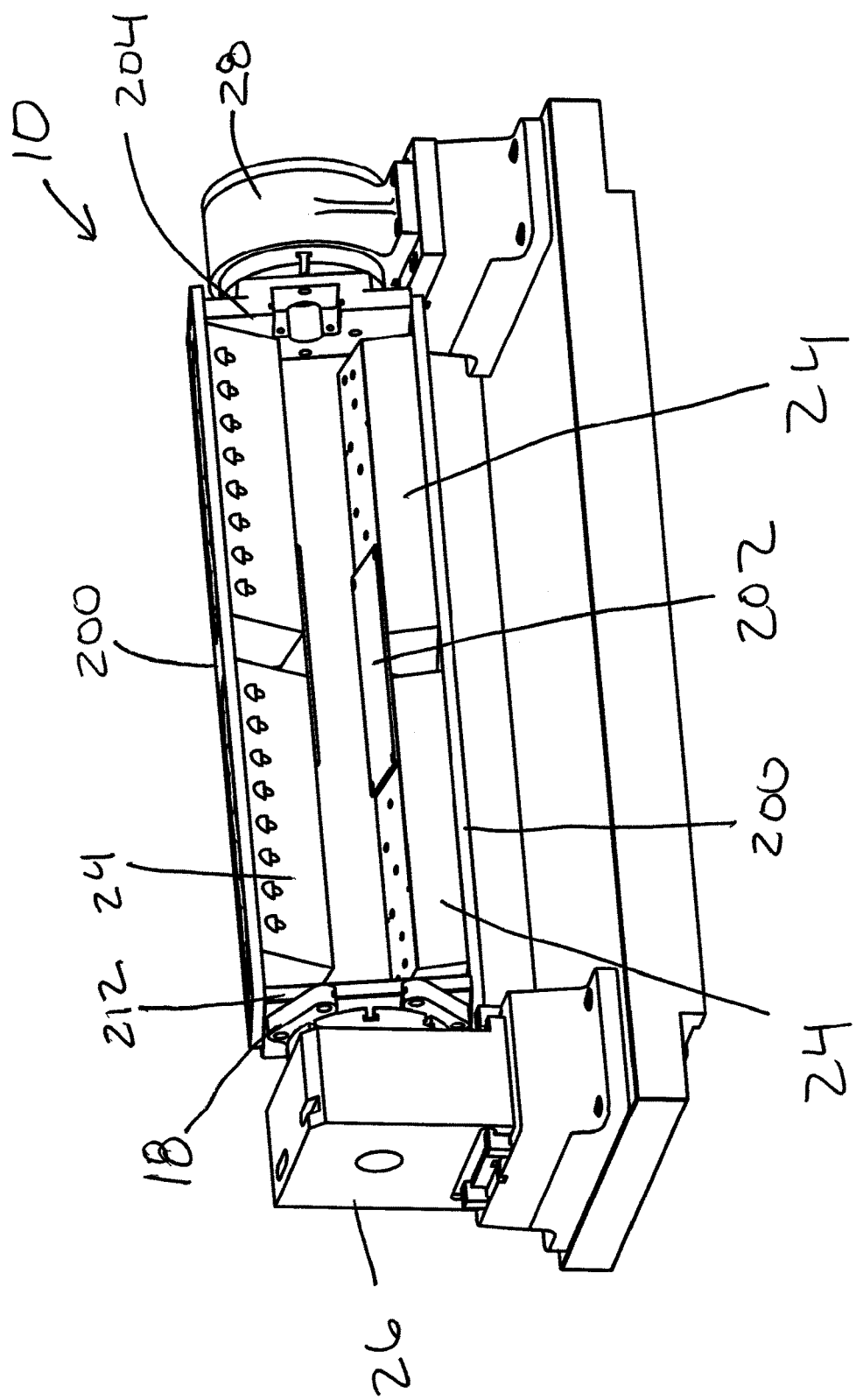
FIG. 21 is a perspective view of a fixture with two head plates according to the present invention.
Figure 22:
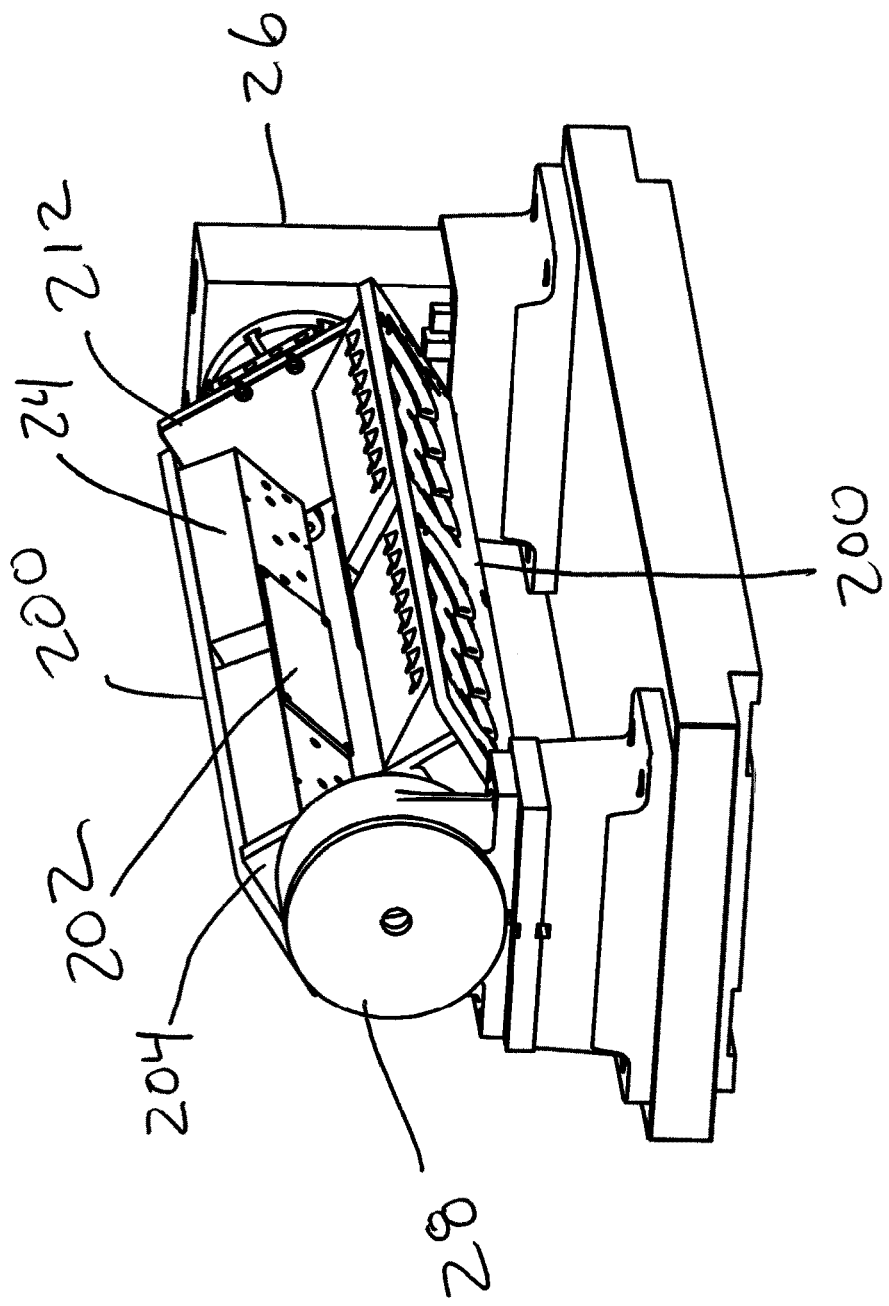
FIG. 22 is a perspective view of a fixture with two head plates according to the present invention.
Figure 23:
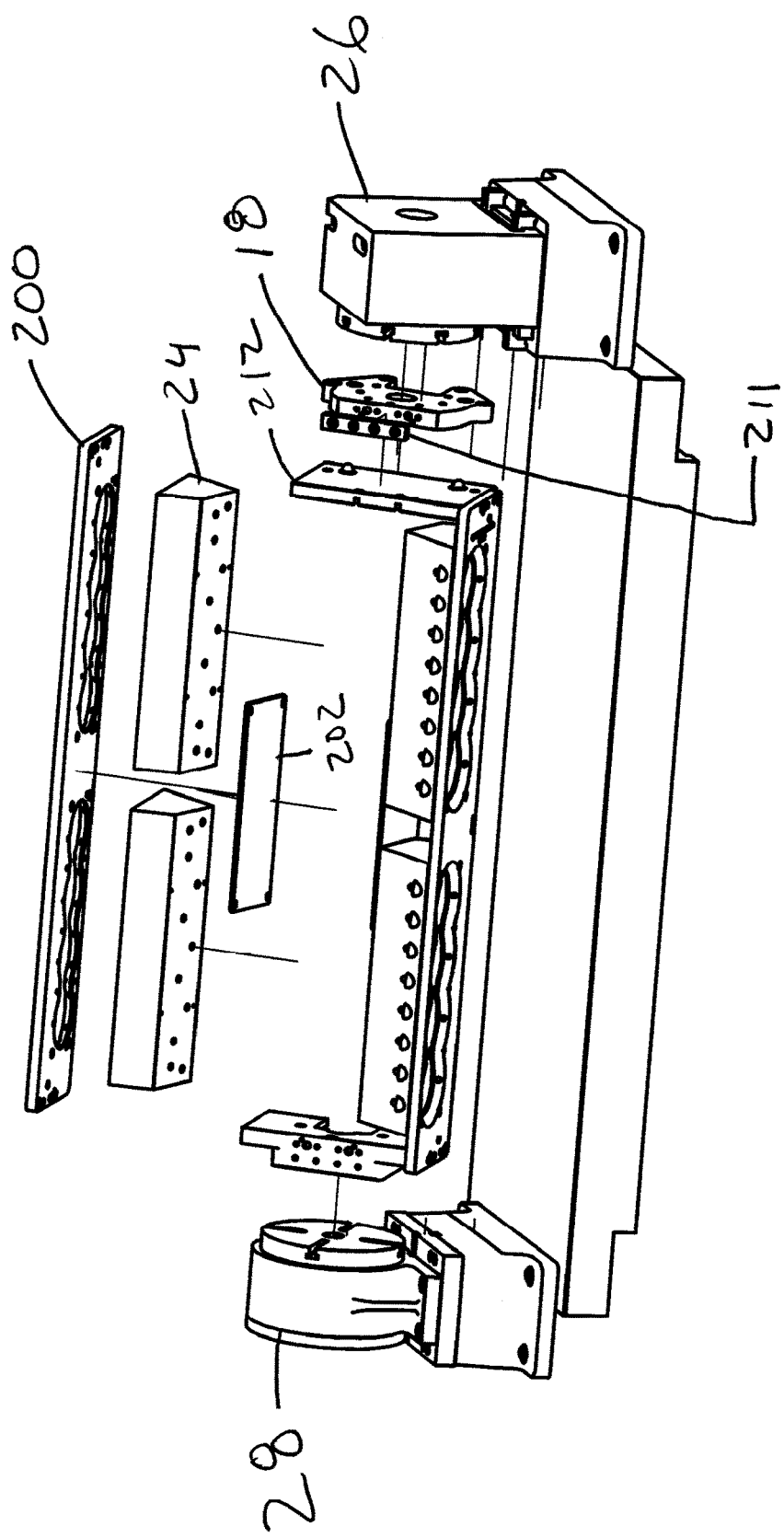
FIG. 23 is a perspective exploded view of a fixture with two head plates according to the present invention.
Figure 24:
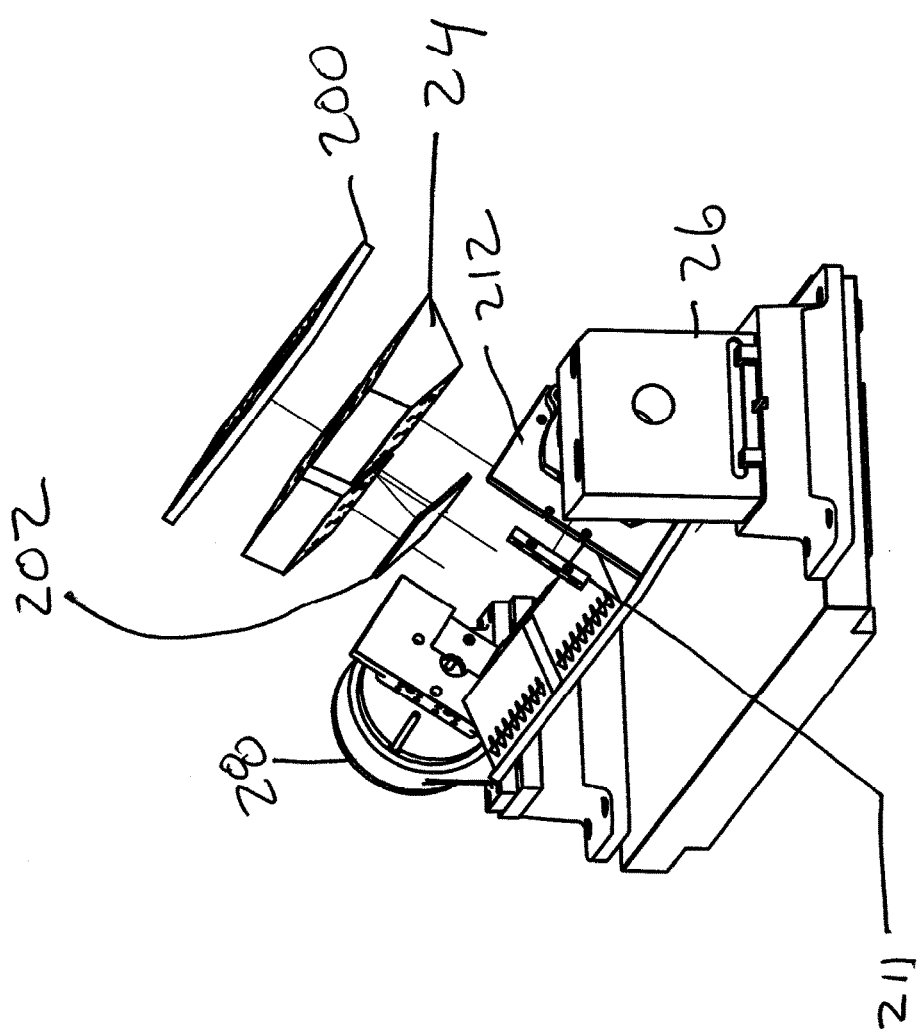
FIG. 24 is a perspective exploded view of a fixture with two head plates according to the present invention.
Figure 25:
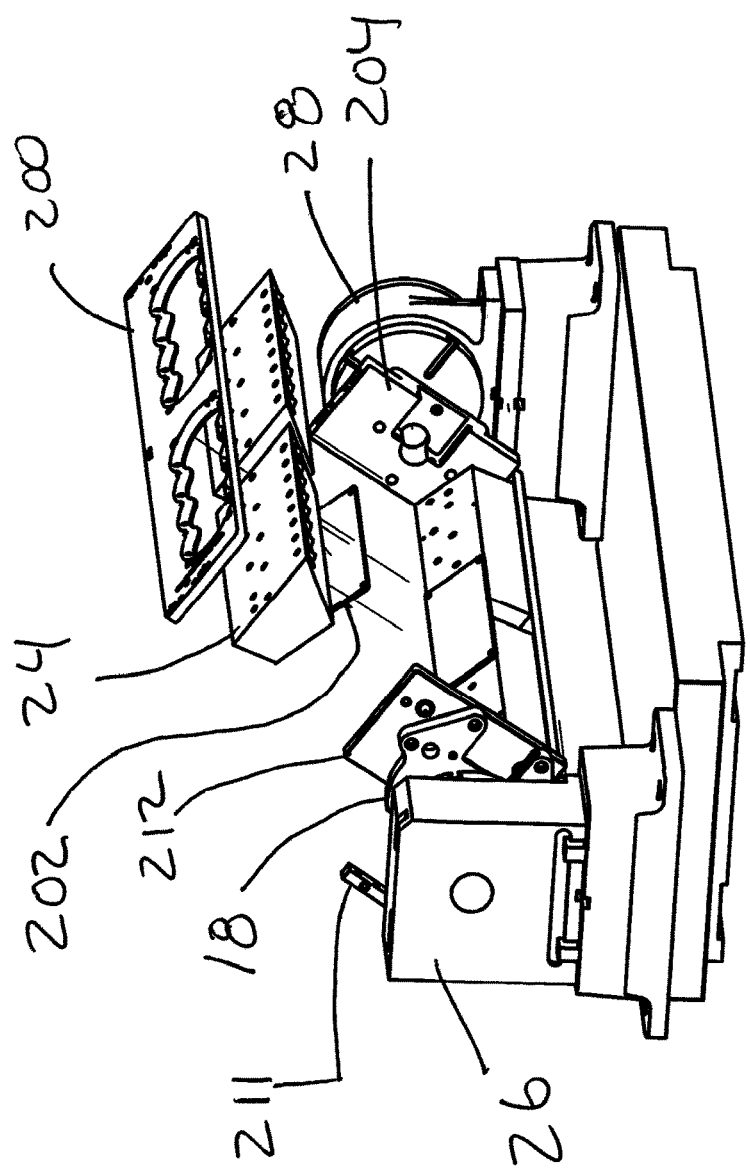
FIG. 25 is a perspective exploded view of a fixture with two head plates according to the present invention.
Figure 26:
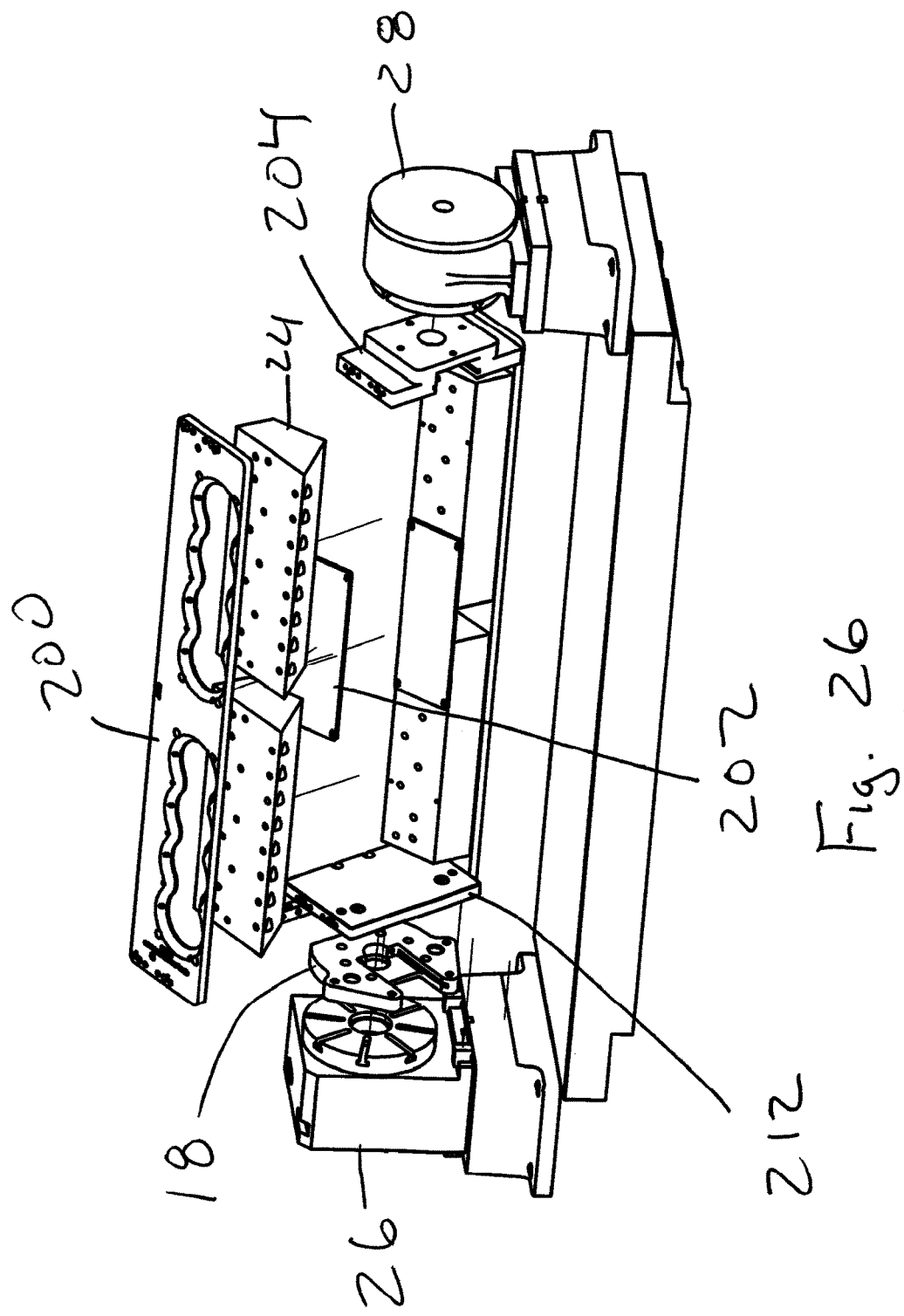
FIG. 26 is a perspective exploded view of a fixture with two head plates according to the present invention.
Figure 27:
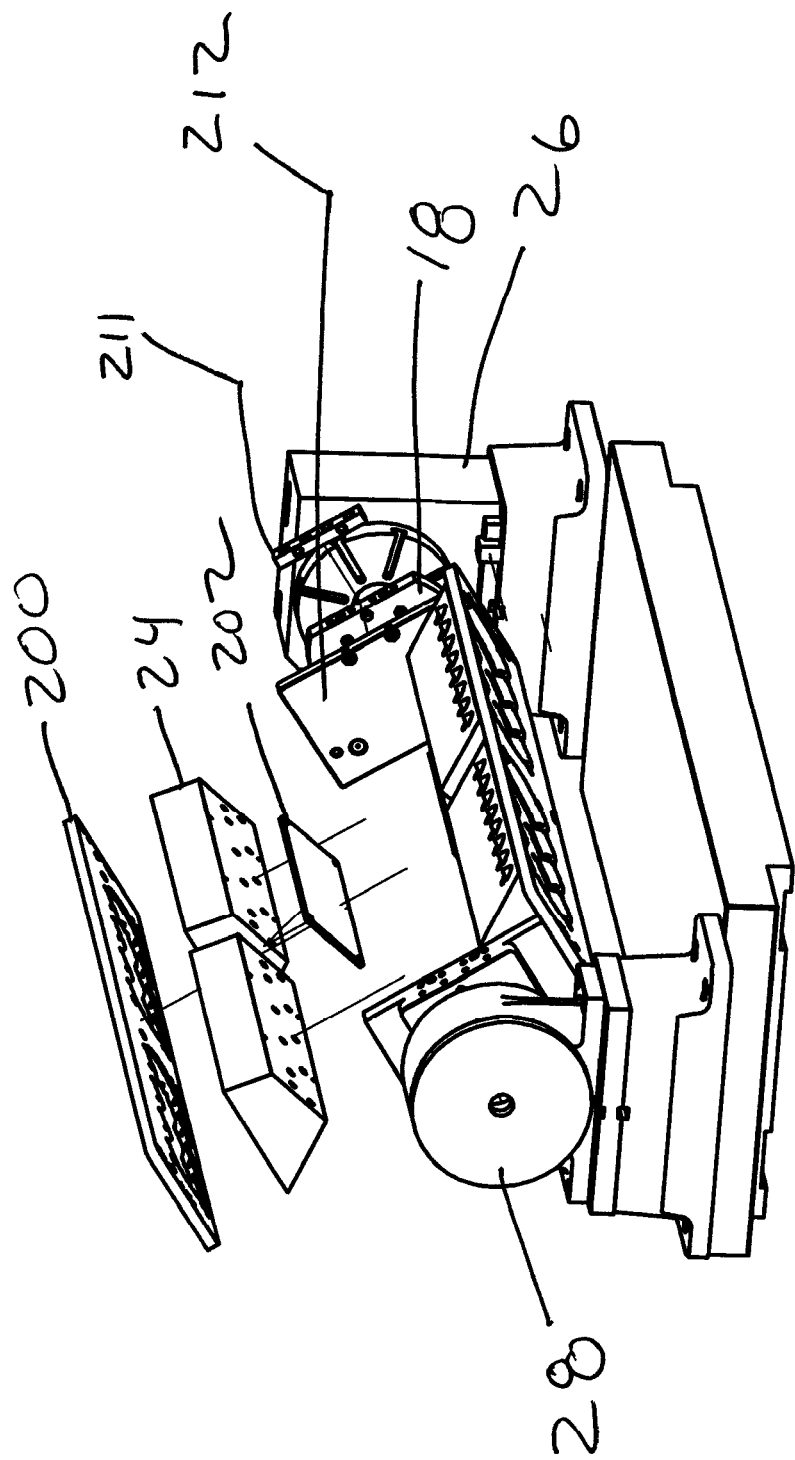
FIG. 27 is a perspective exploded view of a fixture with two head plates according to the present invention.

The tailstock plate 20 attaches to the tailstock 28 and includes bolt holes 116 to bolt the tailstock plate 20 to the tailstock 28, as shown in FIGS. 14-16. The tailstock plate 20 includes reference dowels 118 extending from a head plate surface 120 of the tailstock plate 20. There are bolt holes 122 in the head plate surface 120. The dowels 118 are for receiving the head plate 16 and the bolt holes 122 are for securing the head plate 16 to the head plate surface 120 of the tailstock plate 20, as shown in FIG. 14. The tailstock plate 20 includes a semicircular opening 124 leading to a round opening 126, both which are designed to receive the tailstock end 128 of the bar 32, as shown in FIG. 15. The tailstock plate 20 includes a clamp opening 130 above the semicircular opening 124 of the tailstock plate 20. The tailstock plate 20 includes a clamping plate 132 that has tongues 134 that slide into slots 136 of the clamp opening 130. The clamping plate 132 bolts into place using bolts 138 and threaded holes 140 of the tailstock plate 20. The clamping plate 132 is used to hold the bar 32 in place at the tailstock plate 20, yet allow the bar 32 to rotate about semicircular opening 124 and the round opening 126. FIG. 17 shows the bar 32 mounted to the tailstock plate 20.

The rotary plate 18 and tailstock plate 20 are for the quick change of attaching the block bar 32 with engine block 22 or head plate 16 with cylinder head 24 in place on a milling machine. This allows for the ability to quickly remove or insert the engine block 22 or flip over the rotary plate 18 180 degrees and attach the cylinder head 24. The tailstock plate 20 rotates with the rotary plate 18 when either the block bar 32 or head plate 16 are attached between them, unless the brake is applied. The rotary plate 18 and the sliding clamp plate 106 clamps the block bar 32 precisely in position on the second precision surface 96. The sliding clamp plates 106, 132 of the rotary plate 18 and tailstock plate 20 are what facilitate the quick removal and installation of the block bar 32. The sliding clamp plates 106, 132 can be removed to allow a clear path for removal or installation of the block bar 32. After installation of the block bar 32, the sliding clamp plates 106, 132 are tightened down and secured with bolts 110, 138. This pushes the block bar 32 into position set by the second precision surface 96 of the rotary plate 18. This feature allows the block bar 32 to remain attached to an engine block 22 during installation and removal from the fixture 10, which significantly reduces the time required during installation or removal. The dowels 90, 118 of the rotary plate 18 and tailstock plate 20 align the head plate 16 on the first precise surface 92 of the rotary plate 18, so that the head plate 16 can be precisely secured to the CNC fixture 10. The dowels 90, 118 are what facilitate the quick removal and installation of the head plate 16. This feature allows the head plate 16 to remain attached to the cylinder head 24 during installation and removal from the fixture 10, which significantly reduces the time required during installation or removal. The head plate 16 is placed on the dowels 90, 118 to act as a reference point, so that the head plate 16 is in the same position on the fixture 10 every time it is mounted to the fixture 10.

Specially designed software within the CNC control of the milling machine records and makes use of the known positions of the head plate 18 and the block bar 32, due to the known first precision surface 92 and second precision surface 96. The software switches coordinates between the head plate 16 and the block bar 32 as necessary, maintaining the required geometric coordinates to minimize measuring and setup time. The software makes use of the fact that the center of the semicircular channel of the second precision surface 96 is known in relation to the first precision surface 92 for attaching the head plate 16. The software uses these positional relationships to calculate the positions of features on an installed engine block 22 or cylinder head 24. The software then uses the calculated positions to control the milling machine to perform precision operations on the engine block 22 such as boring and decking and to perform precision operations on cylinder heads 24 such as porting. The key feature of the software is based on the use of known positional relationship of the first precision surface 92 and second precision surface of the rotary plate 96. When engine blocks 22 are being machined, the software knows the positions of the features to be cut on the engine block 22 based on the second precision surface 96 of the semicircular channel of the rotary plate 18. When cylinder heads 24 are being machined, the software knows the positions to be cut based on the first precision surface 92 of the rotary plate 18. The software relies on the first precision surface 92 and second precision surface 96 to be held in a known relationship by the rotary plate 18.

Figure 28:
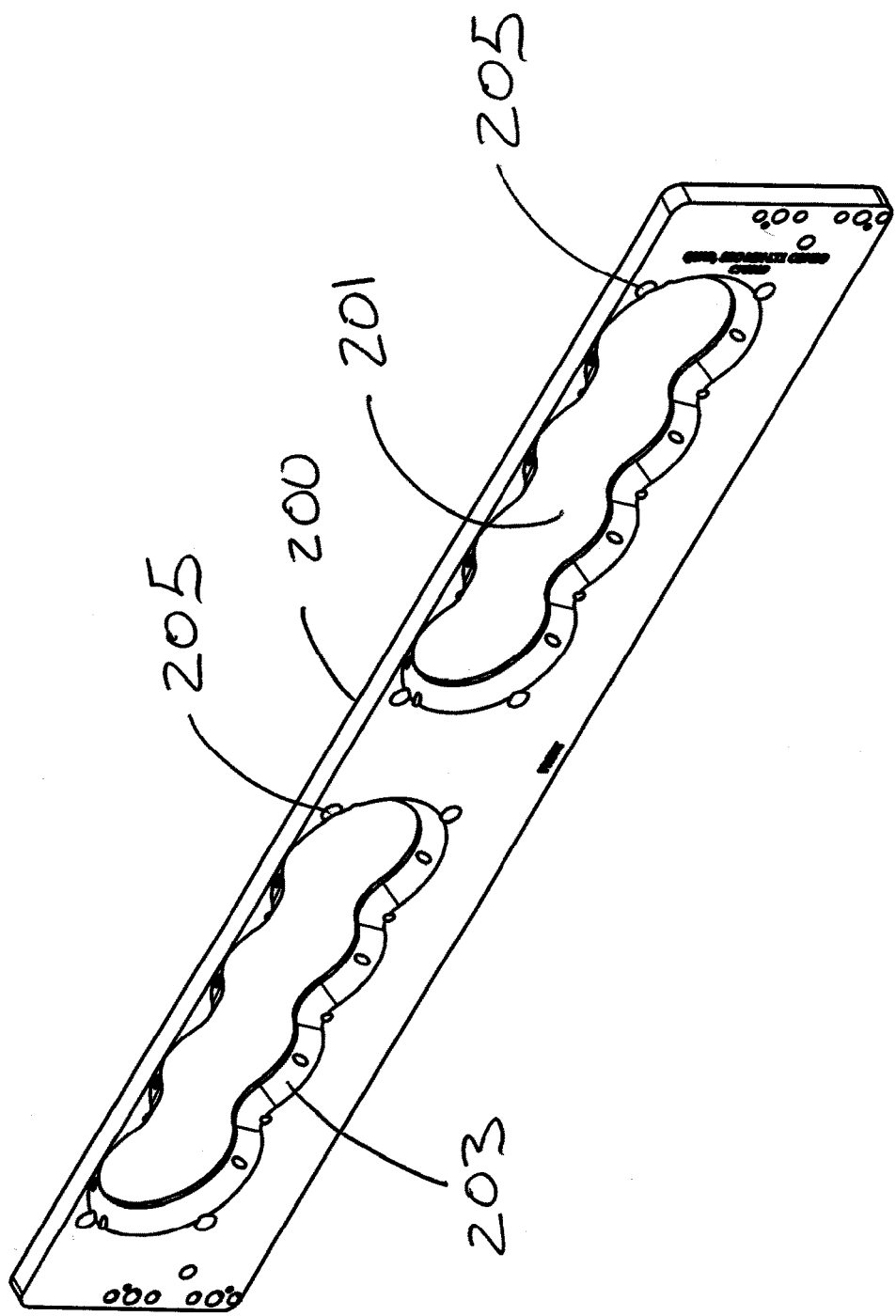
FIG. 28 is a perspective view of a head plate according to the present invention.
Figure 29:
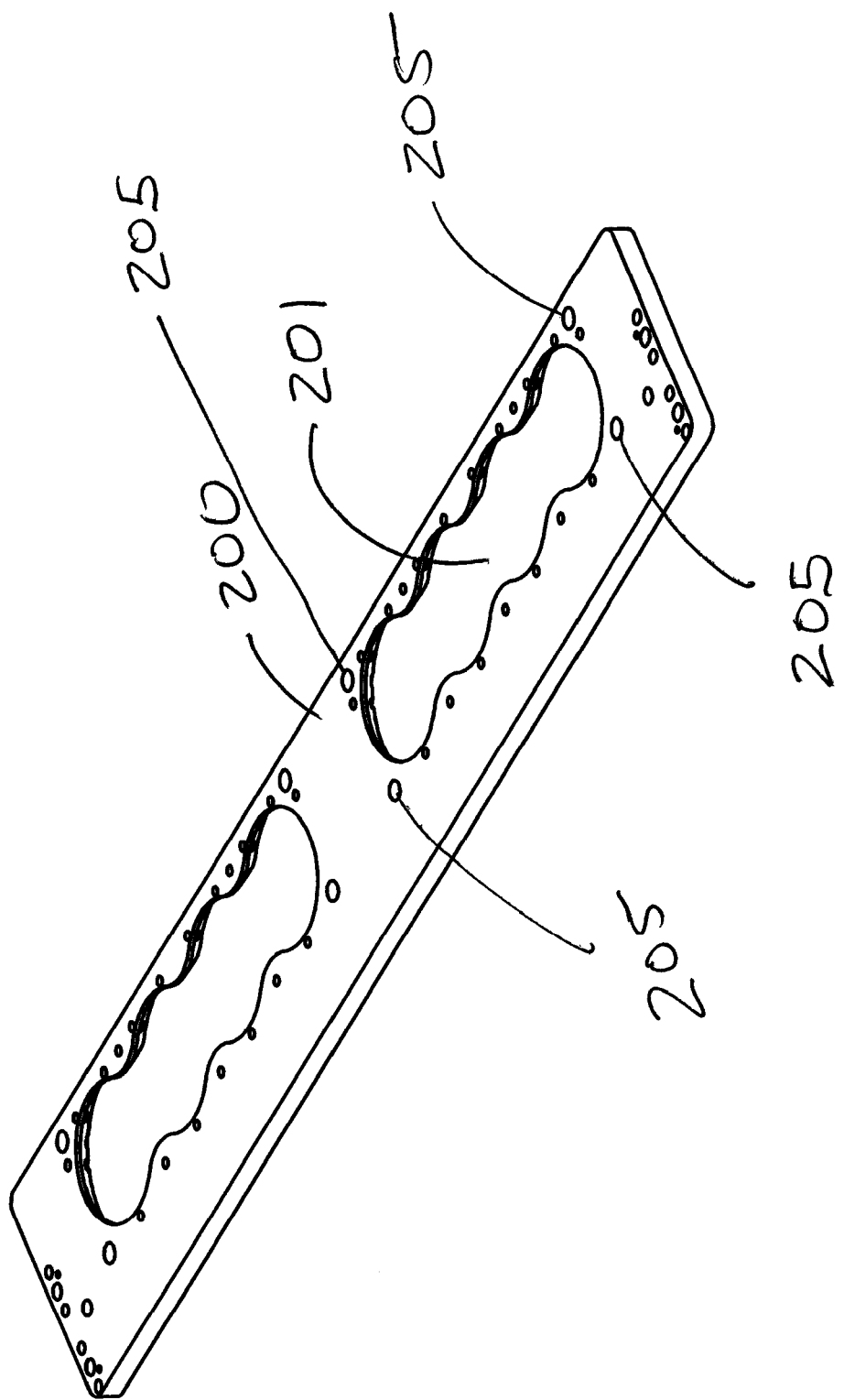
FIG. 29 is a perspective view of a head plate according to the present invention.
Figure 30:
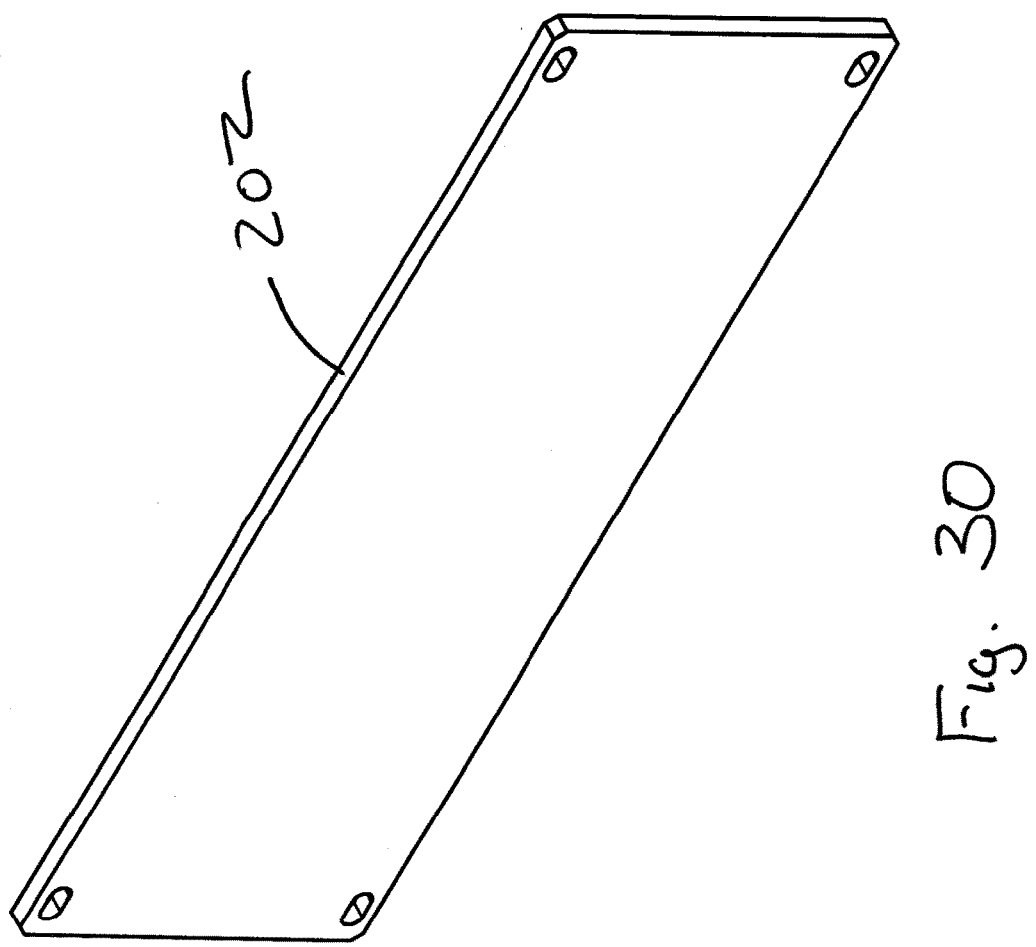
FIG. 30 is a perspective view of a head stiffing plate according to the present invention.
Figure 31:
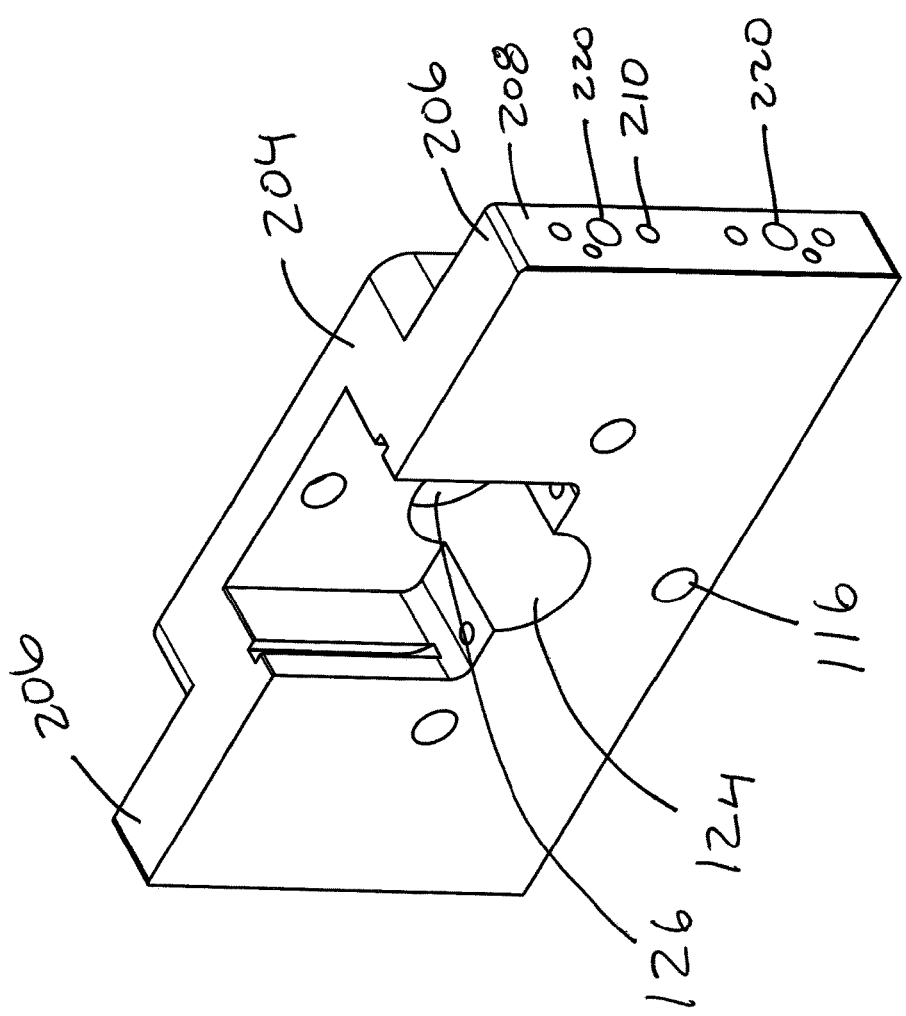
FIG. 31 is a perspective view of a tailstock plate according to the present invention.

FIGS. 19-43 show another embodiment that allows for four individual cylinder heads 24 to be machined on the CNC fixture 10. FIGS. 19-27 show four cylinder heads 24 that attach to head plates 200. The rotary table 26 and tailstock 28 are shown spaced further apart for this embodiment. Each head plate 200 can accommodate two cylinder heads 24. FIGS. 19-22 show two head plates 200 secured between the rotary table 26 and tailstock 28, where each head plate 200 has two cylinder heads 24 attached to each head plate 200. FIG. 28 shows a top view of a top of the head plate 200 and FIG. 29 shows a bottom view of a bottom of the head plate 200. The head plate 200 includes two cylinder head openings 201 to allow machining of the cylinder heads 24. Each cylinder head opening 201 includes a bevel perimeter 203. Each head plate 200 includes bolt holes 205 for attachment of the cylinder heads 24. FIGS. 23-27 show exploded views of the cylinder heads 24 prior to connection to the head plates 200. The top of each cylinder head 24 is bolted to the bottom of the head plate 200. A head stiffing plate 202 is bolted between two cylinder heads 24 and to the bottom of the cylinder heads 24, as shown in FIGS. 19-27 and 30. The head stiffing plate 202 between the two cylinder heads 24 is used to prevent flexure of the head plate 200.

Figure 32:
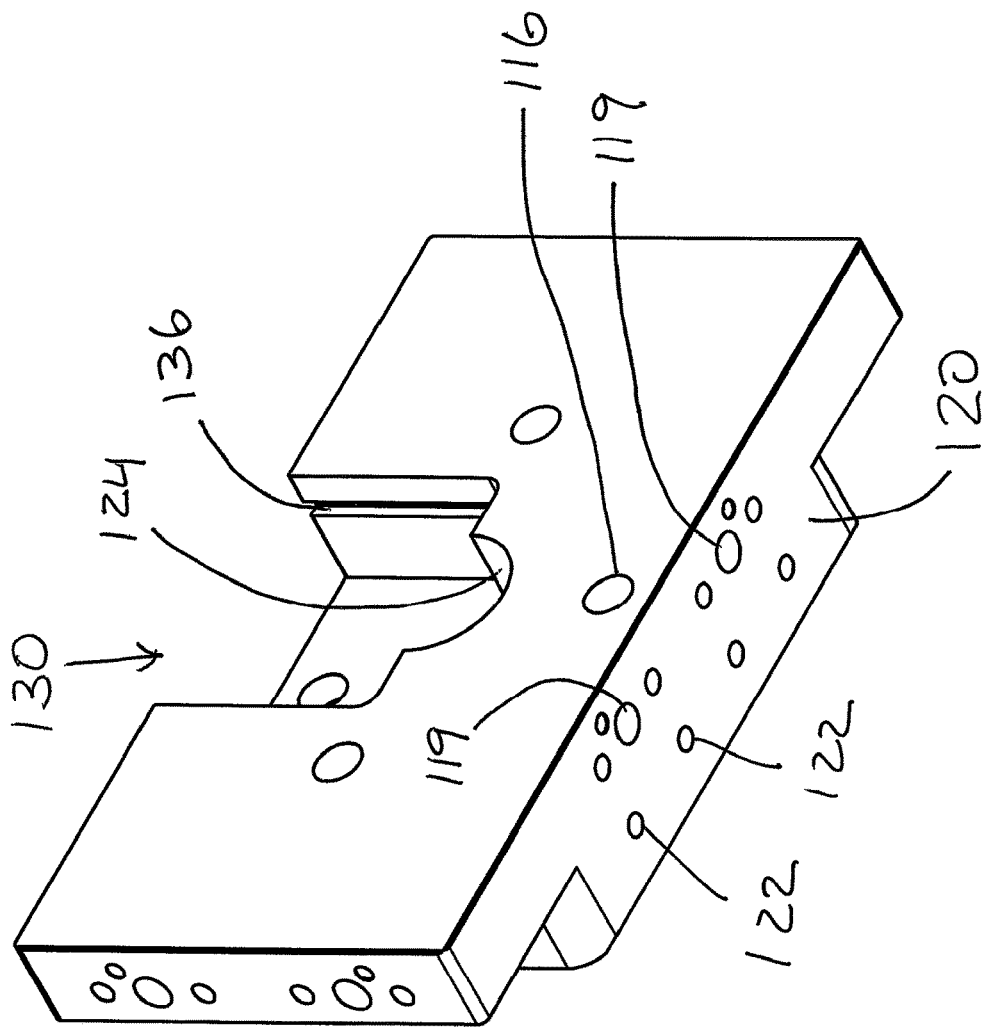
FIG. 32 is a perspective view of a tailstock plate according to the present invention.
Figure 33:
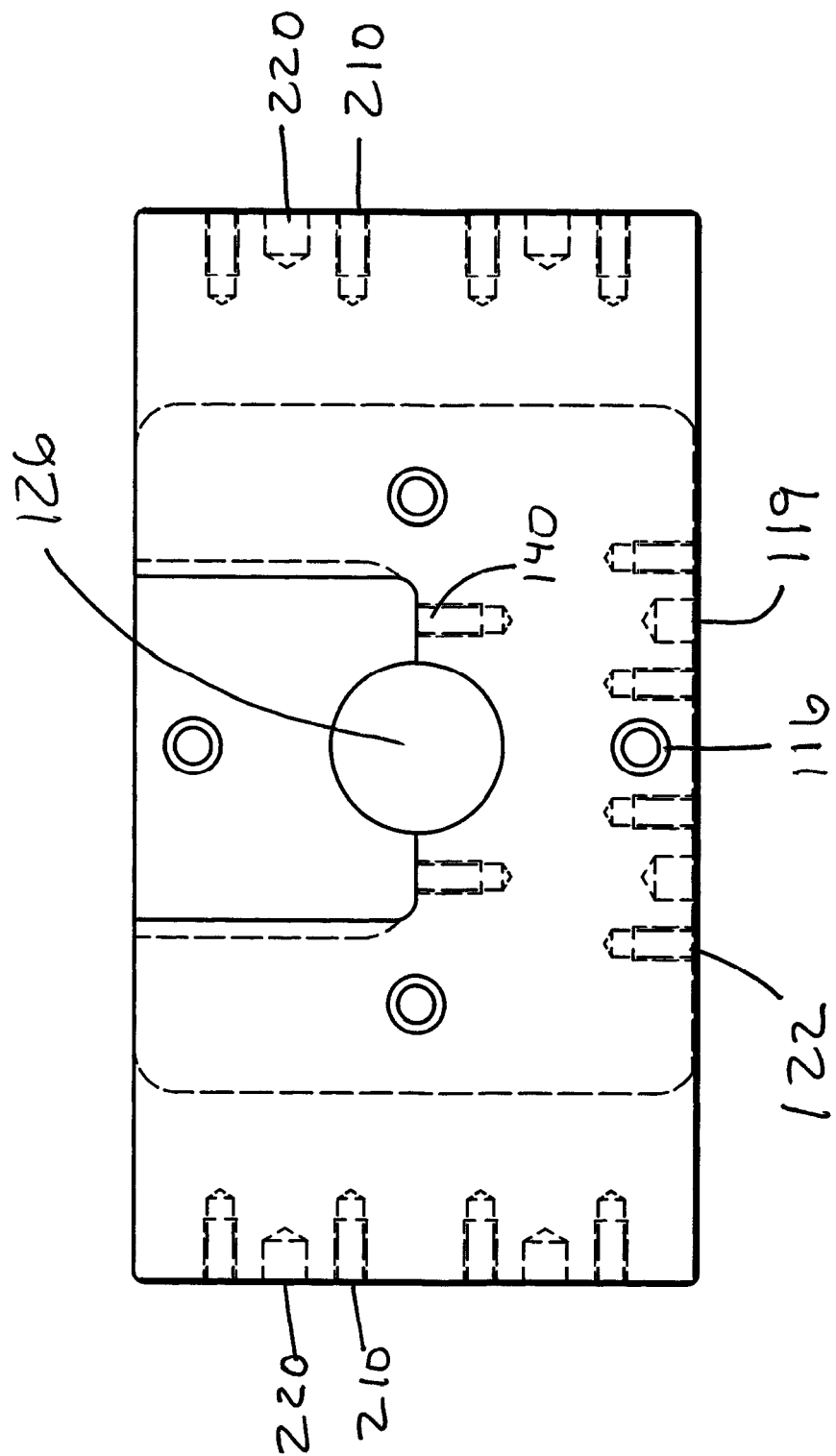
FIG. 33 is a front view of a tailstock plate according to the present invention.
Figure 34:
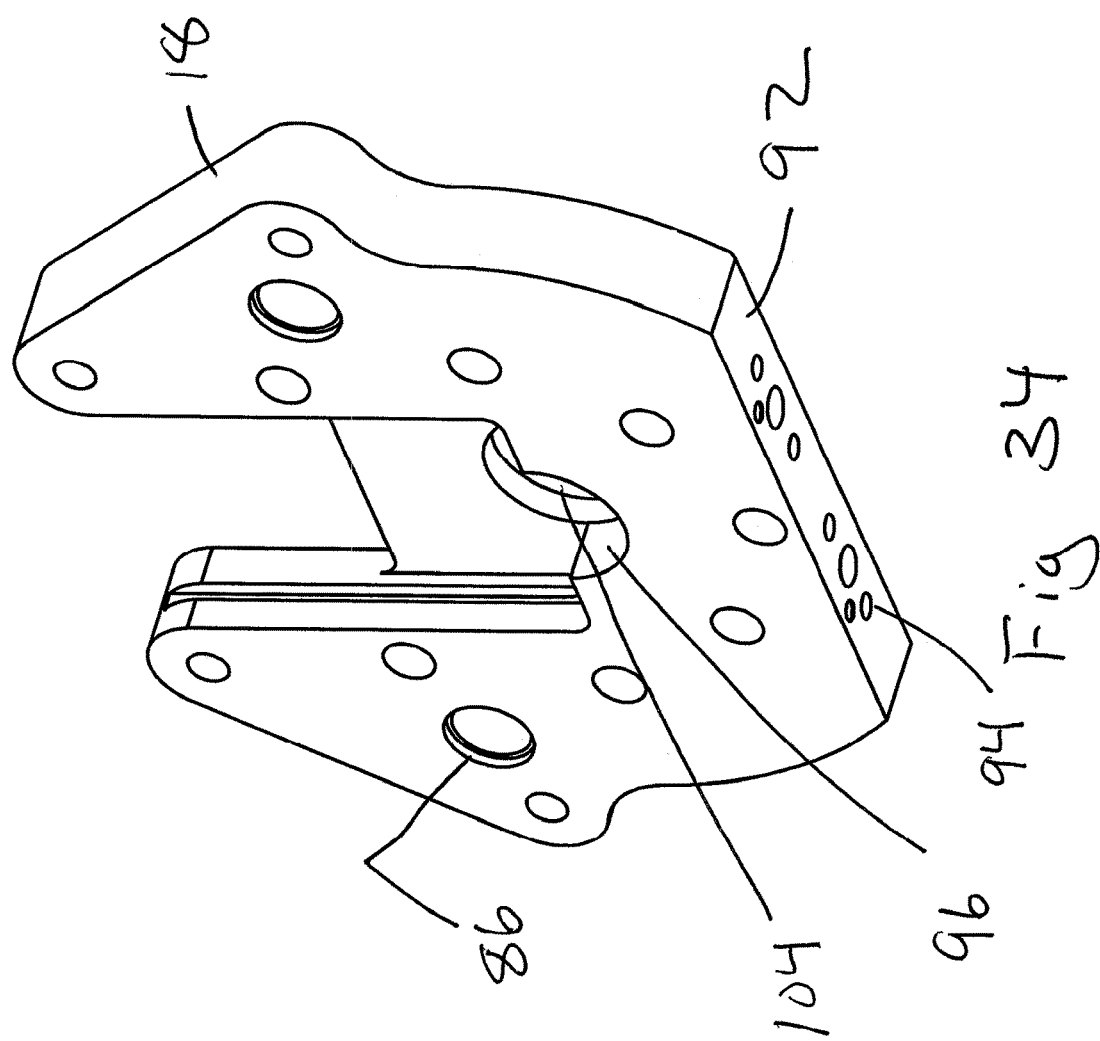
FIG. 34 is a perspective view of a rotary plate according to the present invention.
Figure 35:
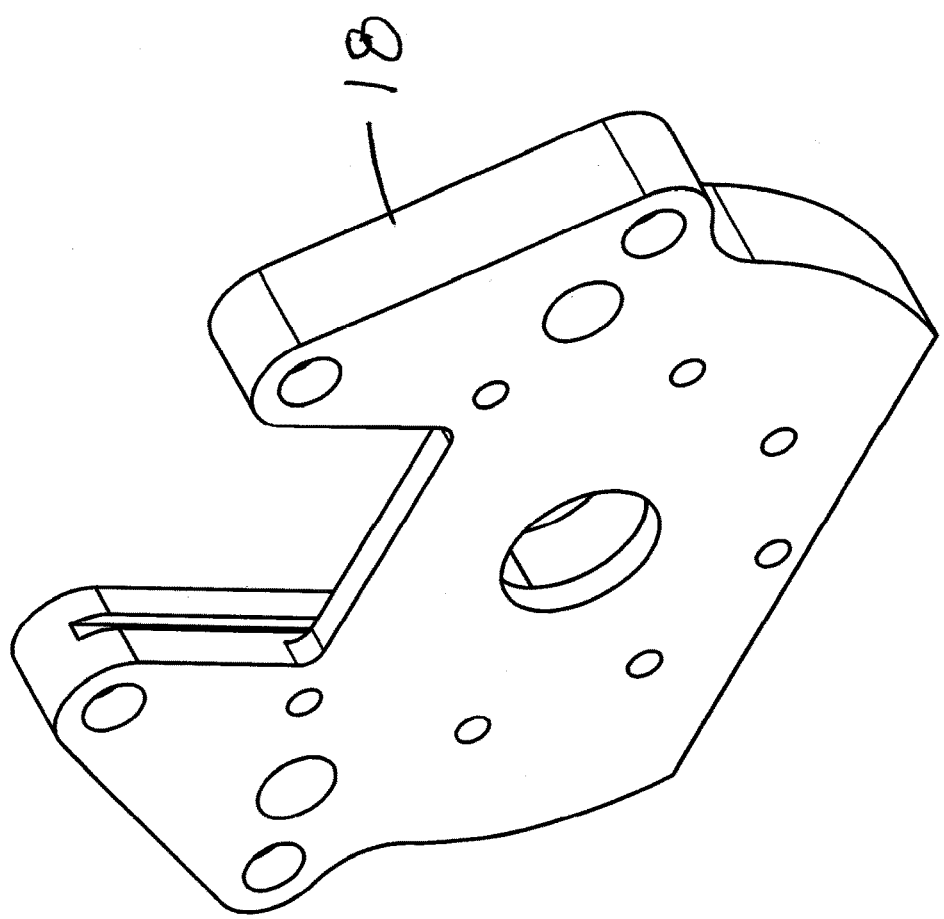
FIG. 35 is a perspective view of a rotary plate according to the present invention.
Figure 36:
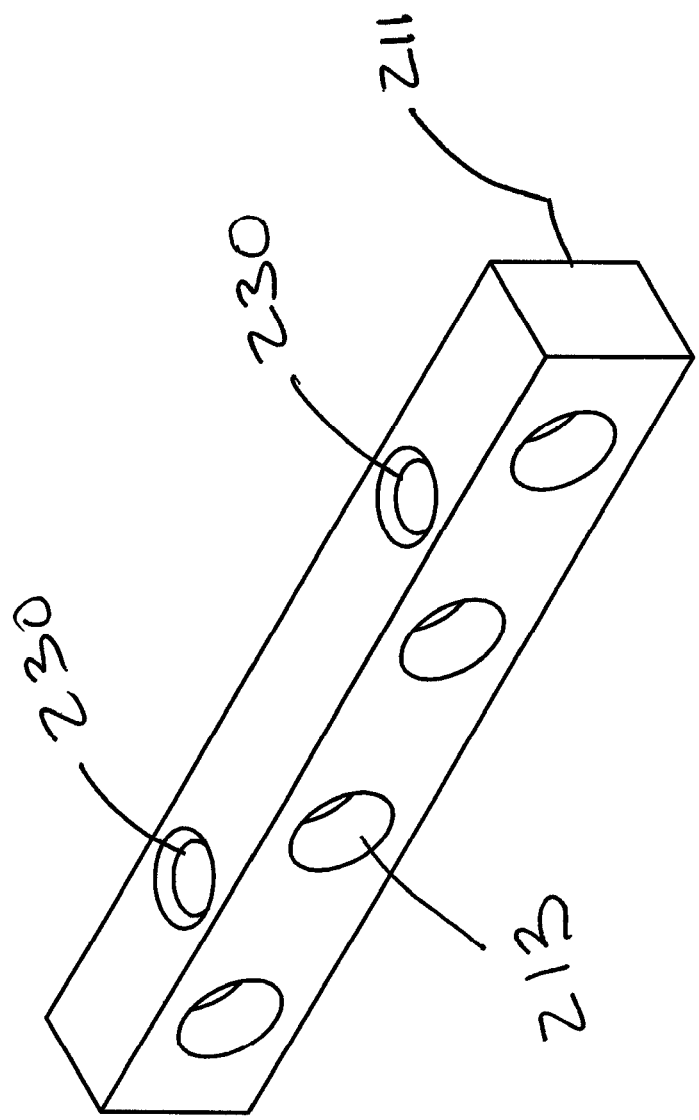
FIG. 36 is a perspective view of a rotary plate extension according to the present invention.
Figure 37:
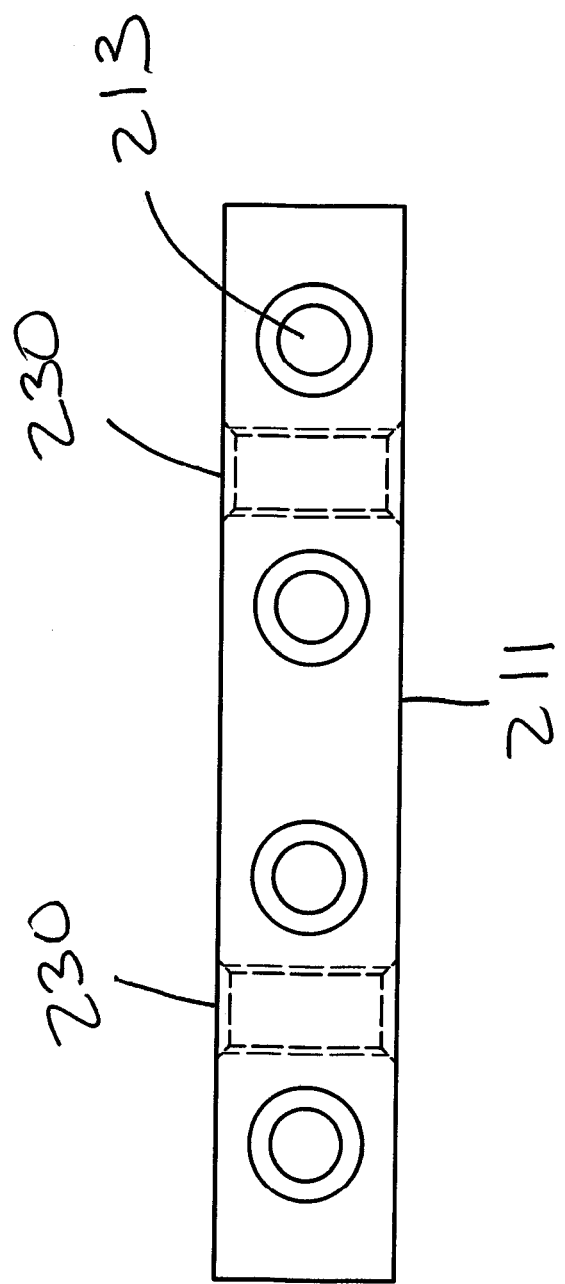
FIG. 37 is a front view of a rotary plate extension according to the present invention.
Figure 38:
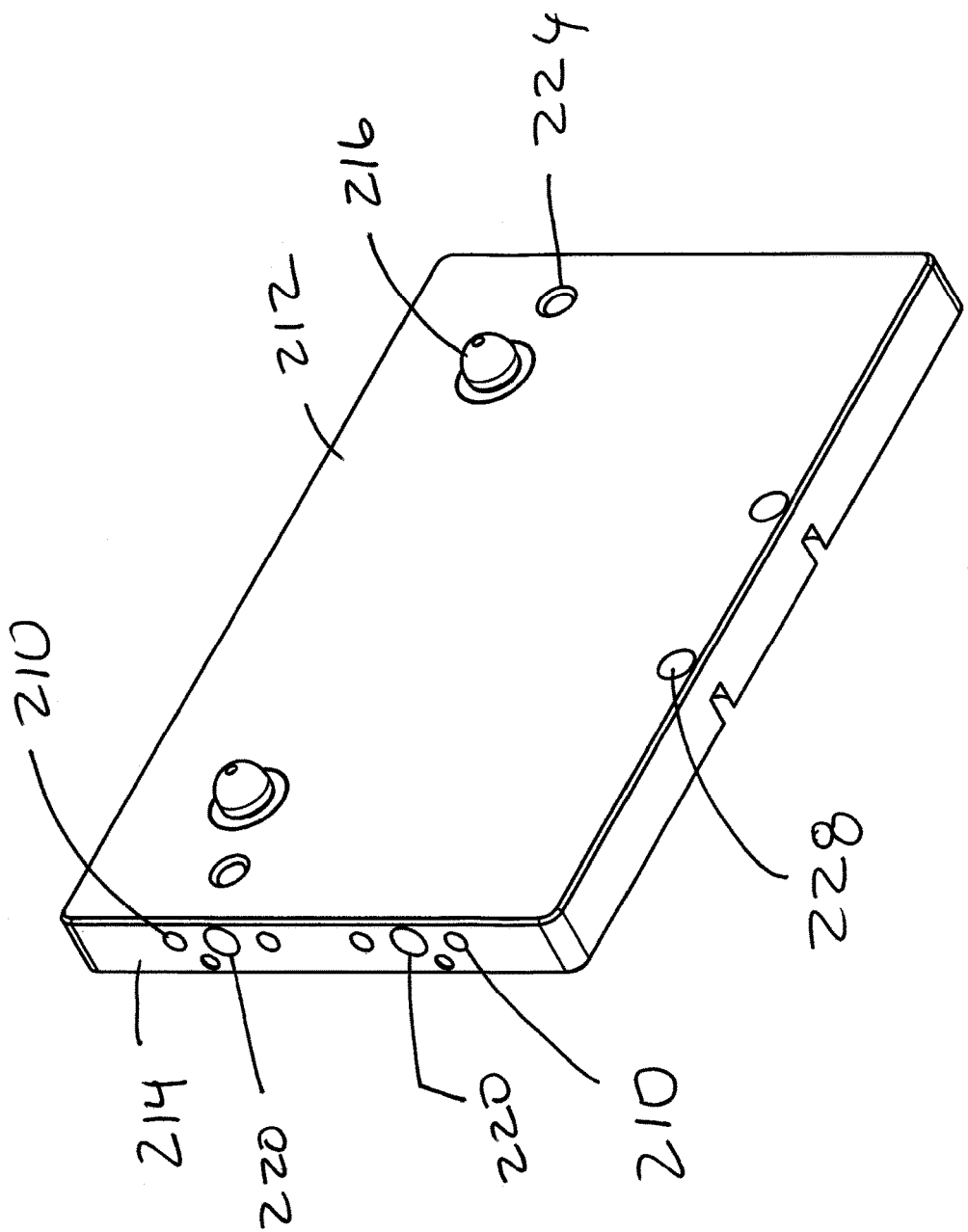
FIG. 38 is a perspective view of a rotary head plate according to the present invention.
Figure 39:
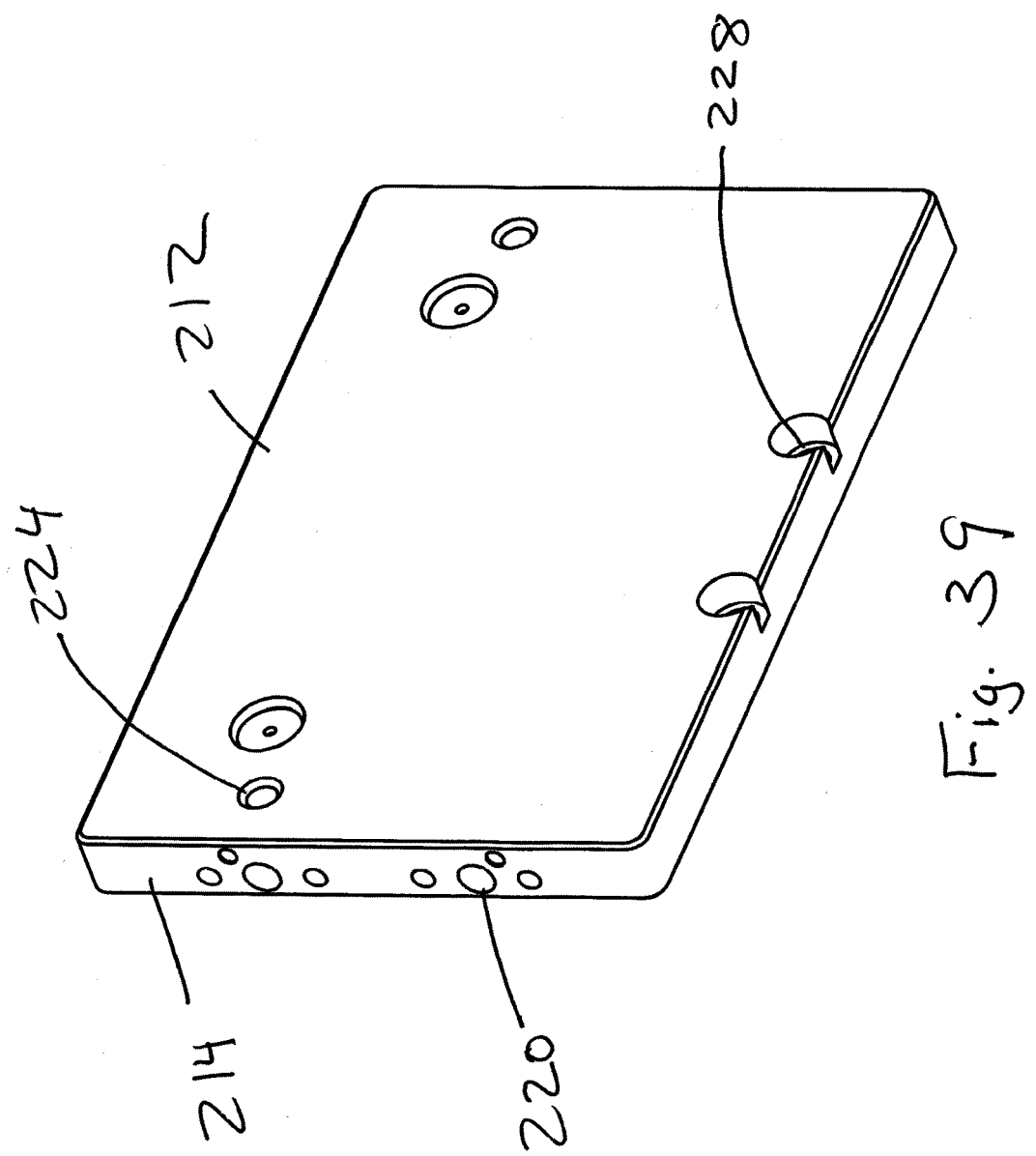
FIG. 39 is a perspective view of a rotary head plate according to the present invention.

FIGS. 19-27 and 31-33 show a tail stock plate 204 connected to the tailstock 28 with elongated sides 206, as compared to tail stock plate 20. The elongated sides 206 provide two head plate surfaces 208, as compared to one surface of the head plate surface 120 of the tailstock plate 20. The elongated sides 206 include threaded bolt holes 210 on the head plate surfaces 208, so that one end of the head plates 200 can be bolted to the tail stock plate 204. The elongated sides 206 also include dowel holes 220 on the head plate surfaces 208 to receive reference dowels. Tail stock plate 204 includes the head plate surface 120 for when the user wishes to use the head plate 16. FIGS. 32-33 show holes 119 to receive the reference dowels 118 of FIGS. 14-15. FIGS. 32-33 show bolt holes 122 in the head plate surface 120. The tailstock plate 204 attaches to the tailstock 28 and includes bolt holes 116 to bolt the tailstock plate 204 to the tailstock 28. The dowels 118 are for receiving the head plate 16 and the bolt holes 122 are for securing the head plate 16 to the head plate surface 120 of the tailstock plate 204. The tailstock plate 204 in FIGS. 32-33 includes the semicircular opening 124 leading to a round opening 126, both which are designed to receive the tailstock end 128 of the bar 32. The tailstock plate 204 includes a clamp opening 130 above the semicircular opening 124 of the tailstock plate 204. The tailstock plate 204 includes slots 136 in the clamp opening 130 to receive the clamping plate 132 of FIG. 15. The clamping plate 132 bolts into place using bolts 138 of FIG. 15 and threaded holes 140 of the tailstock plate 204. The clamping plate 132 is used to hold the bar 32 in place at the tailstock plate 204, yet allow the bar 32 to rotate about semicircular opening 124 and the round opening 126.

Figure 41:
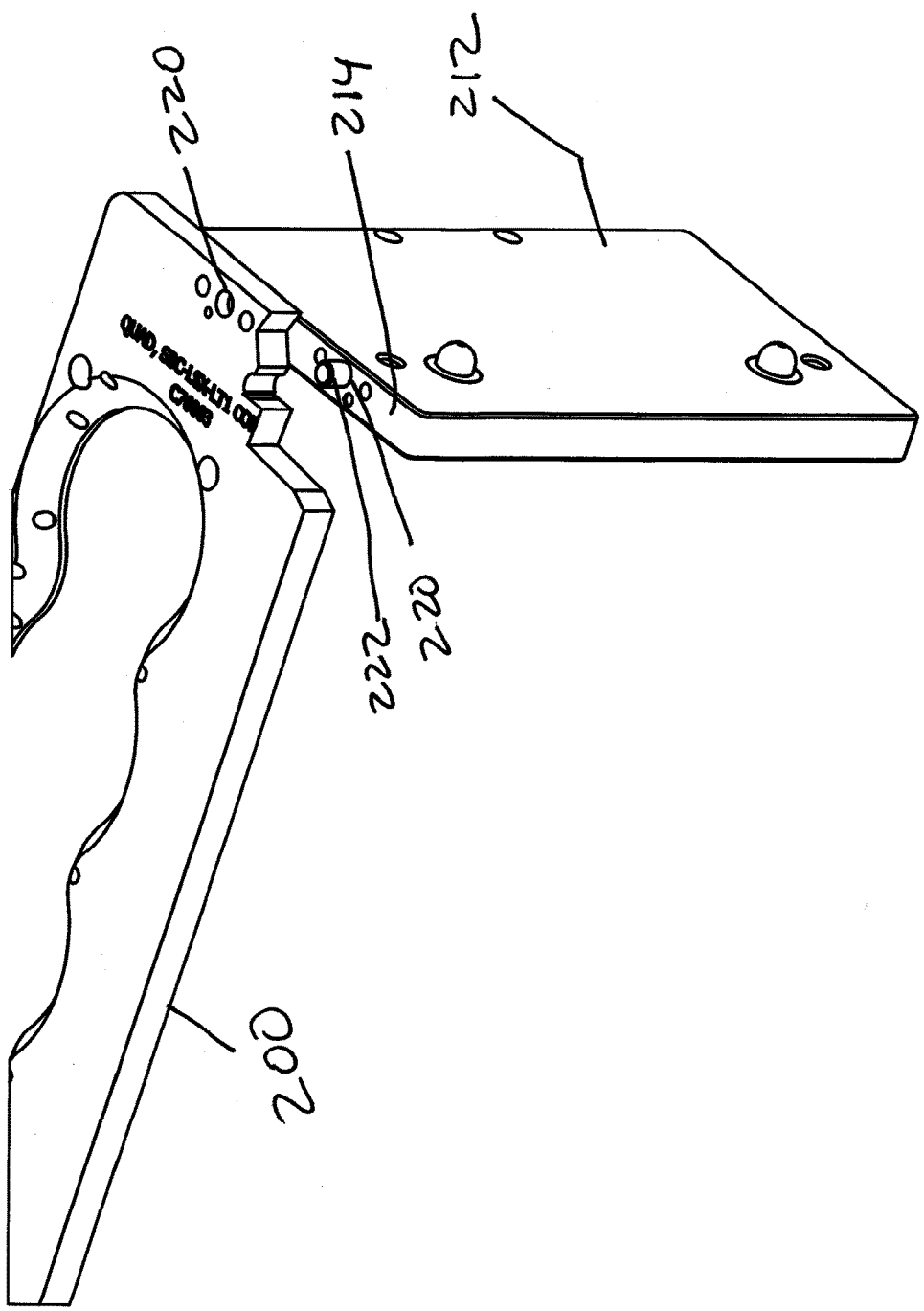
FIG. 41 is a perspective view of a rotary head plate and head plate according to the present invention.
Figure 42:
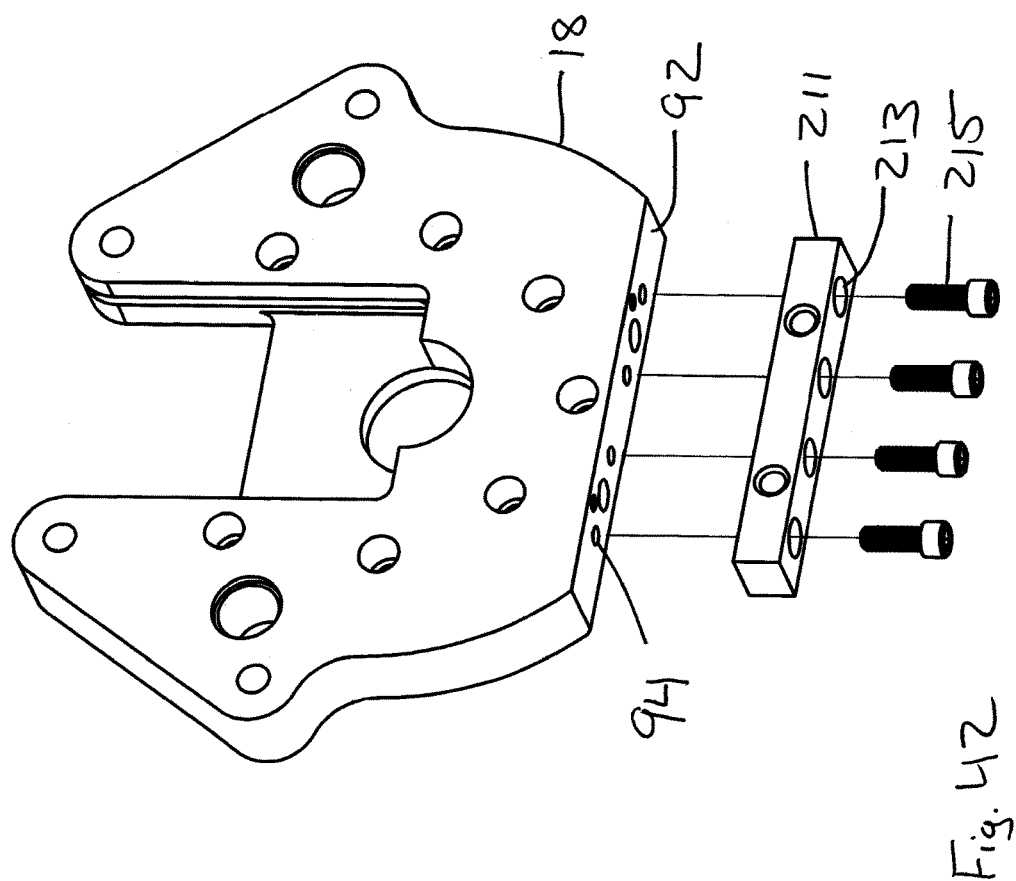
FIG. 42 is a perspective view of a rotary plate according to the present invention.
Figure 43:
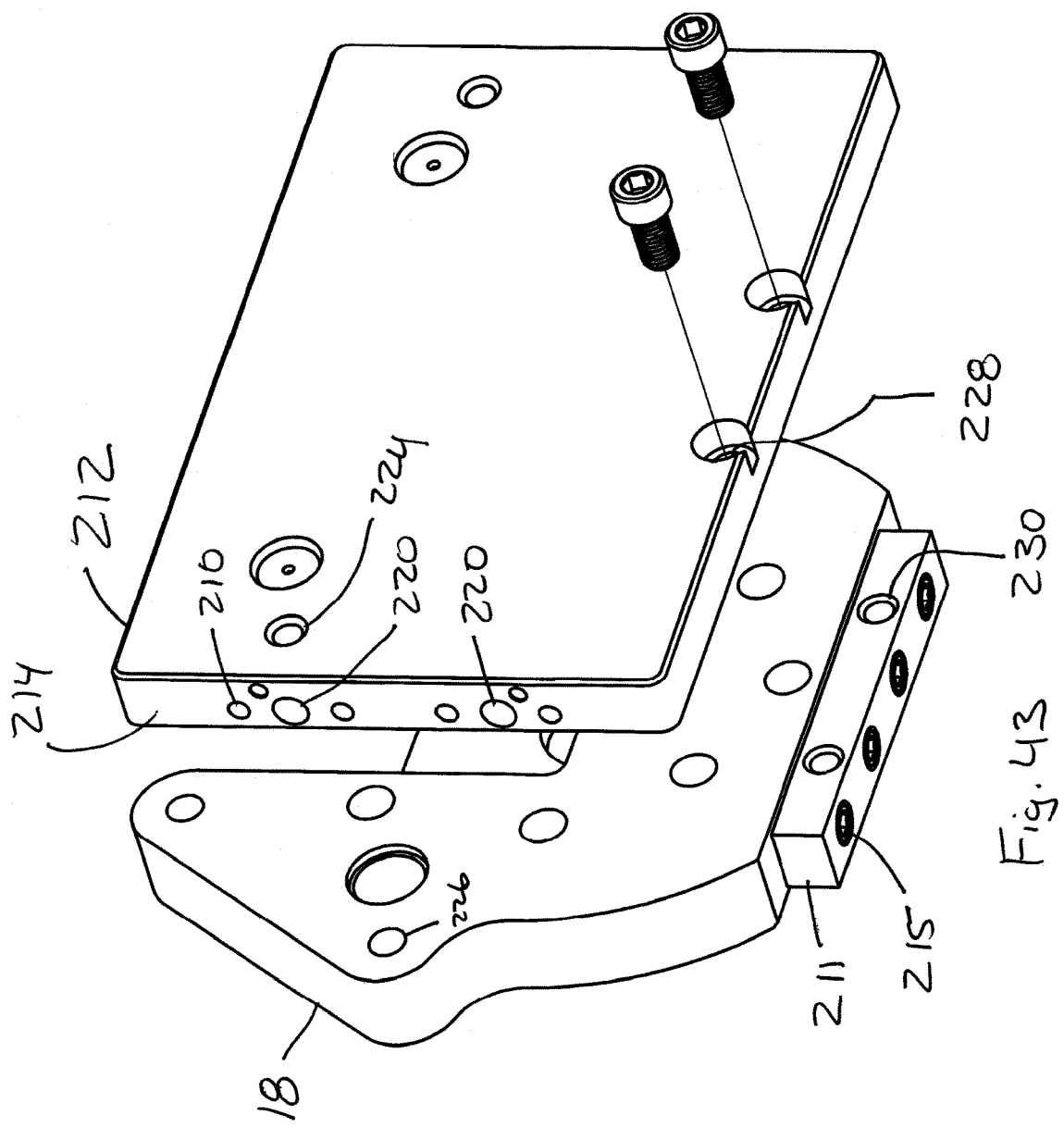
FIG. 43 is a perspective view of a rotary plate and rotary head plate according to the present invention.

FIGS. 19-27 and 34-35 show the rotary plate 18 of FIG. 13 with reference dowels 90 removed. FIGS. 36-37 and 41-43 show a rotary plate extension 211 that attaches to the first precision surface 92. The rotary plate extension 211 includes bolt holes 213 and bolts 215 for attachment of the rotary plate extension 211 to the first precision surface 92 using bolt holes 94, as shown in FIG. 42. The rotary plate extension 211 allows for attachment of a rotary head plate 212 to the rotary plate 18, as shown in FIGS. 19-27 and 43. The rotary head plate 212 includes two precision surfaces 214, which allow the attachment of the head plate 200. The precision surface 214 includes dowel holes 220. The two precision surfaces 214 are used in the same manner the first precision surface 92 is used, as described above for the other embodiments of the present invention. The two precision surfaces 214 include bolt holes 210 for attachment of the head plate 200. The precision surface 214 includes dowel holes 220. The rotary head plate 212 includes alignment pins 216 which insert into alignment pin holes 86 of the rotary plate 18 to provide precision mounting of the rotary head plate 212 to the rotary plate 18. Bolt holes 224 of the rotary head plate 212 are used with bolt holes 226 of the rotary plate 18 to attach the rotary head plate 212 to the rotary plate 18. Bolt holes 228 of the rotary head plate 212 are used with bolt holes 230 of the rotary plate extension 211 to attach the rotary head plate 212 to the rotary plate 18, as shown in FIG. 43.

Figure 40:
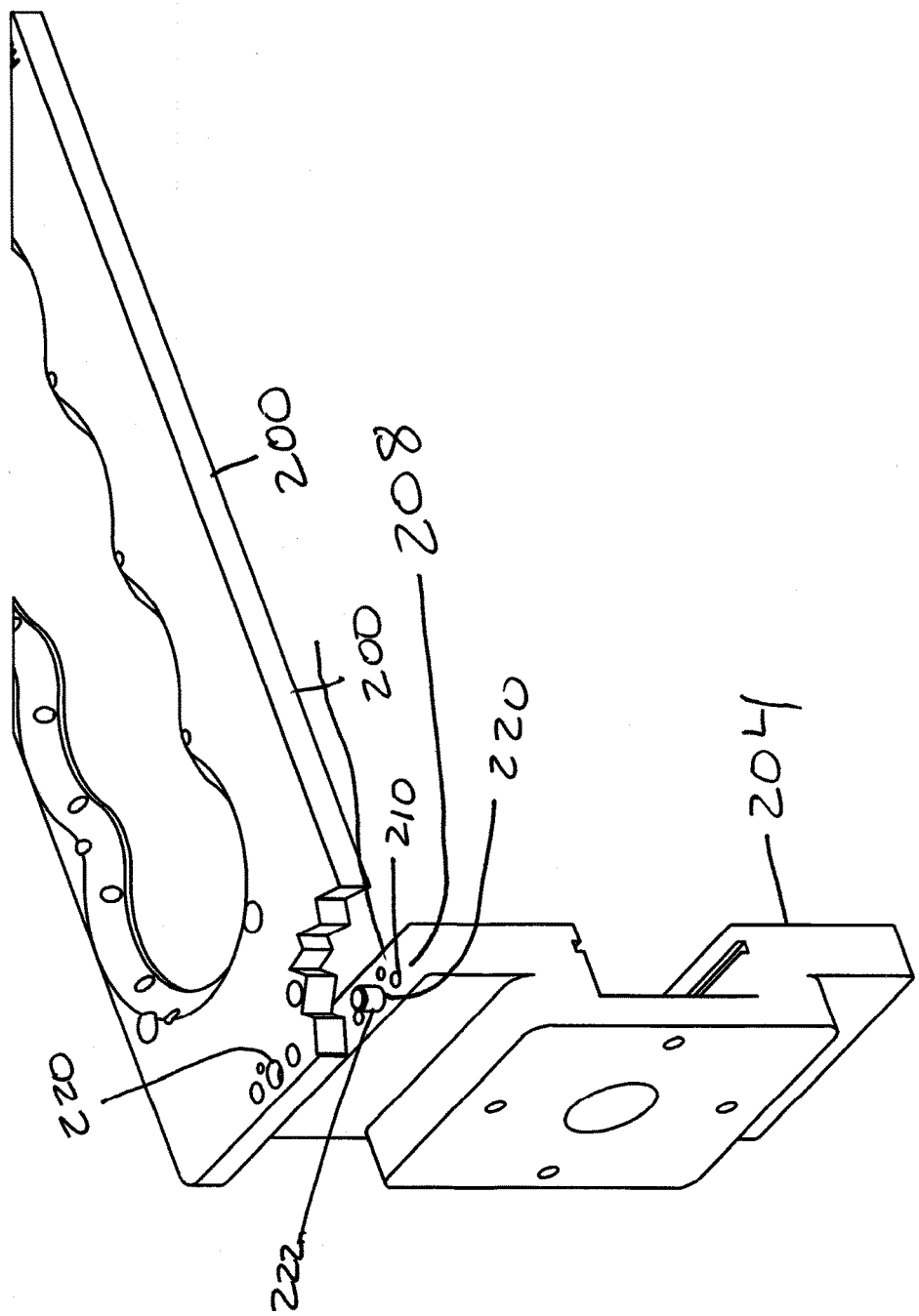
FIG. 40 is a perspective view of a tailstock plate and head plate according to the present invention.

FIG. 40 shows the attachment of the head plate 200 to the head plate surface 208 of the tail stock plate 204. The head plate surface 208 includes dowel holes 220 to receive reference dowels 222. The head plate 200 also includes dowel holes 220 to receive the reference dowels 222. FIG. 41 shows the attachment of the head plate 200 to the precision surface 214 of the rotary head plate 212. The precision surface 214 includes dowel holes 220 to receive reference dowels 222. The head plate 200 also includes dowel holes 220 to receive the reference dowels 222. The reference dowels 222 are used as a reference point during machining of the cylinder heads 24.

While different embodiments of the invention have been described in detail herein, it will be appreciated by those skilled in the art that various modifications and alternatives to the embodiments could be developed in light of the overall teachings of the disclosure. Accordingly, the particular arrangements are illustrative only and are not limiting as to the scope of the invention that is to be given the full breadth of any and all equivalents thereof.

I claim:

1. A fixture for a milling machine to position and manipulate related work pieces, comprising:
    a rotary head plate, said rotary head plate having a first precision surface and a second precision surface;
    a first sub fixture, said first sub fixture being powered to rotate said rotary head plate, said rotary head plate mounted to said first sub fixture such that said rotary head plate is rotated by said first sub fixture;
    a second sub fixture, said second sub fixture being able to freely rotate with said rotary head plate when rotated;
    a tailstock plate mounted to said second sub fixture, said tailstock plate freely rotatable with said rotary head plate when said rotary head plate is rotated; said tailstock plate having a first precision surface and a second precision surface;
    a first head plate attached to and between said first precision surface of said rotary head plate and said first precision surface of said tailstock plate, said first head plate adapted to receive two cylinder heads, said first head plate including at least one cylinder head opening that is a through opening through said first head plate;
    a second head plate attached to and between said second precision surface of said rotary head plate and said second precision surface of said tailstock plate, said second head plate adapted to receive two cylinder heads, said second head plate including at least one cylinder head opening that is a through opening through said second head plate; and
    said tailstock plate capable of rotating with said rotary plate due to attachment of said first head plate and said second head plate.

2. The fixture of claim 1, further including a head stiffing plate for each of said head plates adapted to be mounted between and directly to the two cylinder heads attached to each of said head plates.

3. The fixture of claim 1, wherein said first precision surface and said second precision surface of said rotary head plate and said first precision surface and said second precision surface of said tailstock plate each includes at least one dowel extending outward to receive each said head plate and wherein each said head plate includes at least one dowel hole on each end of each said head plate to receive said at least one dowel so that each said head plate rests on a known position on said first precision surfaces and said second precision surfaces to provide a known location of the cylinder heads attached to said first head plate and said second head plate by knowing said first precision surfaces and said second precision surfaces and said dowels.

4. The fixture of claim 1, further including a computer based control connected to said first sub fixture to control rotation of said rotary head plate and where said computer based control maintains said locations of said first precision surfaces and said second precision surfaces as reference points.

5. A fixture for a milling machine to position and manipulate related work pieces that are assembled together, comprising:
    a rotary plate, said rotary plate having a first precision surface and a second precision surface;
    a first sub fixture, said first sub fixture being powered to rotate said rotary plate, said rotary plate mounted to said first sub fixture such that said rotary plate is rotated by said first sub fixture;
    a second sub fixture, said second sub fixture being able to freely rotate with said rotary plate when rotated and said second sub fixture including a brake to prevent free rotation;
    a tailstock plate mounted to said second sub fixture, said tailstock plate freely rotatable with said rotary plate when said rotary plate is rotated;
    one of a first plate fixture and a second plate fixture, said first plate fixture mounted between said rotary plate and said tailstock plate, said first plate fixture mounted to said first precision surface of said rotary plate at one end and said first plate fixture mounted to said tailstock at a second end, said first plate fixture adapted to receive a first work piece that intended to be assembled with a second work piece; said second plate fixture mounted between said rotary plate and said tailstock plate, said second plate fixture mounted to said rotary plate at said second precision surface of said rotary plate; said second plate fixture having an additional fixture mounted to said second precision surface and said tailstock; said second plate fixture adapted to receive said second work piece to be assembled with said first work piece;
    where finished first and second work pieces mate together when milling is finished, and where a relationship of locations of said first precision surface and said second precision surface are known during milling to precisely locate in space where the first and second work pieces are mounted in said fixture due to the known locations of said first precision surface and said second precision surface allow for quick installation of the first and second work pieces between said first sub fixture and said second sub fixture;

said tailstock plate including a first surface for mounting of said first plate fixture with the first work piece, said tailstock plate including a second surface for mounting of said additional fixture of said second plate fixture with the second work piece, said tailstock plate capable of rotating with said rotary plate due to attachment of either work piece; and a rotary head plate as an accessory to be attached to said rotary plate, said rotary head plate having a first head plate precision surface and a second head plate precision surface;

said tailstock plate having a first precision head plate surface and a second precision head plate surface;

a first head plate to replace one of said first plate fixture and said second plate fixture as an accessory that attaches to and between said first precision head plate surface of said rotary head plate and said first precision head plate surface of said tailstock plate, said first head plate adapted to receive two cylinder heads, said first head plate including at least one cylinder head opening;

a second head plate to replace one of said first plate fixture and said second plate fixture as an accessory that attaches to and between said second precision head plate surface of said rotary head plate and said second precision head plate surface of said tailstock plate, said second head plate adapted to receive two cylinder heads, said second head plate including at least one cylinder head opening; and said tailstock plate capable of rotating with said rotary plate when said first head plate and said second head plate are attached to said tailstock plate and said rotary head plate.

6. The fixture of claim 5, wherein said second plate fixture is a block bar assembly adapted to receive an engine block as the second work piece and wherein said block bar mounts to said second precision surface of said rotary plate and said surface of said tailstock plate.

7. The fixture of claim 6, wherein said block bar assembly includes a block mount and a precise round bar, said block mount attached to said rotary plate and adapted to mount to a face of the engine block, said precise round bar adapted to mount in the crankshaft area of the engine block such that the engine block rests on said precise round bar.

8. The fixture of claim 7, wherein said block mount includes adjustment arms adapted to mount to the engine block, said adjustment arms adapted to adjust for bolt positions and surface of the engine block.

9. The fixture of claim 7, wherein said precision round bar extends beyond said block mount to engage said second precision surface of said rotary plate to provide said known location of the second work piece by knowing said location of said second precision surface and said precision round bar when engaged.

10. The fixture of claim 9, wherein said second precision surface of said rotary plate is a semicircle to receive said precise round bar that extends beyond said block mount.

11. The fixture of claim 10, wherein said rotary plate includes a clamp opening to receive said precise round bar that extends beyond said block mount, said clamp opening allowing for quick install and removal of said precise round bar to said second precision surface; wherein said rotary plate includes a clamping plate which mounts in said clamp opening to secure said precise round bar that extends beyond said block mount to said second precision surface such said precise round bar rotates with said rotary plate when rotated.

12. The fixture of claim 11, further including a computer based control connected to said first sub fixture to control rotation of said rotary plate and where said computer based control maintains said locations of said first precision surface and said second precision surface as reference points, which also allows for quick install and removal of either the first and second work piece.

13. The fixture of claim 10, wherein said first precision surface of said rotary plate and said first surface of said tailstock plate each includes at least one dowel extending outward to receive said head plate and wherein said head plate includes at least one dowel hole on each end of said head plate to receive said at least one dowel of each of said first precision surface of said rotary plate and said first surface of said tailstock plate so that said head plate rests on a known position on the first precision surface to provide said known location of the first work piece by knowing said location of said first precision surface and said at least one dowel of said rotary plate.

14. The fixture of claim 10, wherein said second surface of said tailstock plate is a semicircle to receive said precise round bar.

15. The fixture of claim 14, wherein said second surface of said tailstock plate is a semicircle to receive said precise round bar, wherein said tailstock plate includes a clamp opening to receive said precise round bar, said clamp opening of said tailstock plate allowing for quick install and removal of said precise round bar to said second surface tailstock plate; wherein said tailstock plate includes a clamping plate which mounts in said clamp opening of said tailstock plate to secure said precise round bar at said tailstock plate.

16. The fixture of claim 15, further including a computer based control connected to said first sub fixture to control rotation of said rotary plate and where said computer based control maintains said locations of said first precision surface and said second precision surface as reference points, which also allows for quick install and removal of either the first and second work piece.

17. The fixture of claim 5, wherein said first plate fixture is a head plate adapted to receive a cylinder head as the first work piece and wherein said head plate mounts to said first precision surface of said rotary plate and said first surface of said tailstock plate.

18. The fixture of claim 17, further including a computer based control connected to said first sub fixture to control rotation of said rotary plate and where said computer based control maintains said locations of said first precision surface and said second precision surface as reference points, which also allows for quick install and removal of either the first and second work piece.

19. The fixture of claim 5, further including a computer based control connected to said first sub fixture to control rotation of said rotary plate and where said computer based control maintains said locations of said first precision surface and said second precision surface as reference points, which also allows for quick install and removal of either the first and second work piece.

* * * * *